United States Patent [19]

Matner et al.

[11] Patent Number: 5,073,488

[45] Date of Patent: Dec. 17, 1991

[54] RAPID METHOD FOR DETERMINING EFFICACY OF A STERILIZATION CYCLE AND RAPID READ-OUT BIOLOGICAL INDICATOR

[75] Inventors: Richard R. Matner, St. Paul; William E. Foltz, Cottage Grove; Lewis P. Woodson, Eagan, all of Minn.

[73] Assignee: Minnesota Mining and Manufacturing Company, St. Paul, Minn.

[21] Appl. No.: 277,305

[22] Filed: Nov. 29, 1988

[51] Int. Cl.$^5$ .......................... C12Q 1/00; C12Q 1/25
[52] U.S. Cl. .......................................... 435/31; 435/38
[58] Field of Search ..................................... 435/31, 38

[56] References Cited

U.S. PATENT DOCUMENTS

| | | | |
|---|---|---|---|
| 2,854,384 | 9/1958 | Beakley et al. | 195/54 |
| 3,239,429 | 3/1966 | Menolasino et al. | 195/54 |
| 3,346,464 | 10/1967 | Ernst | 195/54 |
| 3,440,144 | 4/1969 | Andersen | 195/103.5 |
| 3,551,295 | 12/1970 | Dyer | 195/103.5 |
| 3,585,112 | 6/1971 | Ernst | 195/103.5 |
| 3,752,743 | 8/1973 | Henshilwood | 195/127 |
| 3,796,635 | 3/1974 | Delente | 195/65 |
| 3,846,242 | 11/1974 | Ernst | 195/103.5 |
| 4,011,139 | 3/1977 | Horwath et al. | 195/65 |
| 4,162,942 | 7/1979 | Gunther | 435/17 |
| 4,284,719 | 8/1981 | Agerhem et al. | 435/18 |
| 4,291,122 | 9/1981 | Orelski | 435/31 |
| 4,304,869 | 12/1981 | Dyke | 435/296 |
| 4,348,209 | 9/1982 | Murtaugh et al. | 23/232 R |
| 4,416,984 | 11/1983 | Wheeler, Jr. | 435/31 |
| 4,448,548 | 5/1984 | Foley | 364/160 |
| 4,461,837 | 7/1984 | Karle et al. | 435/296 |
| 4,528,268 | 7/1985 | Andersen et al. | 435/31 |
| 4,579,823 | 4/1986 | Ryder | 435/296 |
| 4,580,682 | 4/1986 | Gorski et al. | 206/569 |
| 4,591,554 | 5/1986 | Koumura et al. | 435/18 |
| 4,596,773 | 6/1986 | Wheeler, Jr. | 435/31 |
| 4,603,108 | 7/1986 | Bascomb | 435/34 |
| 4,883,641 | 11/1989 | Wicks et al. | 422/50 |

FOREIGN PATENT DOCUMENTS

| | | |
|---|---|---|
| 0000063 | 6/1978 | European Pat. Off. |
| 86/05206 | 9/1986 | PCT Int'l Appl. |
| 1547747 | 2/1978 | United Kingdom |
| 2128204A | 4/1983 | United Kingdom |

OTHER PUBLICATIONS

Singleton et al., "Proteins from Thermophilic Microorganisms", Bacteriol Rev. 37, 320–42, (1973).

Wisdon et al., "Membranes of *Bacillus Stoarothermophilus:* Factors Affecting Protoplast Stability and Thermostability of Alkaline Phosphatase and Reduced Nicotinamide Adenine Dinucleotide Oxidase", J. Bacteriol 114, 1336–45 (1973).

Roth, M., "Fluorimetric Assay of Enzymes", Methods of Biochemical Analysis, vol. 17, pp. 189–285.

"Fluorescence in Enzymology", Quantitative Assay of Enzymes, pp. 312–348.

Snyder, A. P. et al., "Pattern Recognition Analysis of In Vivo Enzyme-Substrate Fluorescence Velocities in Microorganism Detection and Identification", Appl. Environ. Microbiol., vol. 51, No. 5, pp. 969–977 (1986).

Laurence, D. J. R., "Fluorescence Techniques for the Enzymologist", Techniques for Characterization of Proteins, pp. 174–212.

(List continued on next page.)

*Primary Examiner*—Robert A. Wax
*Assistant Examiner*—M. P. Woodward
*Attorney, Agent, or Firm*—Gary L. Griswold; Walter N. Kirn; Jennie G. Boeder

[57] ABSTRACT

A rapid method of determining the efficacy of a sterilization cycle, and an indicator adapted to perform such method, comprising subjecting to the sterilization cycle a source of active enzyme having activity which correlates with the viability of a microorganism commonly used to monitor sterilization, and incubating the enzyme source, following the completion of the sterilization cycle, with an effective amount of a substrate system capable of reacting with any residual active enzyme to produce a detectable enzyme-modified product.

25 Claims, 4 Drawing Sheets

OTHER PUBLICATIONS

Warth, A. D., "Heat Stability of Bacillus cereus Enzymes within Spores and in Extracts", Journal of Bacteriology, vol. 143, No. 1, pp. 27-34 (1980).

Yutani, K. et al., "Comparison of Thermostable α-Amylases from B. stearothermophilus Grown at Different Temperatures", J. Biochem., 74, pp. 573-579 (1973).

Suzuki, Y. et al., "Assignment of A p-Nitrophenyl α-D-Glucopyranosidase of Bascillus Stearothermophilus ATCC 12016 to a Novel Exo-α-1,4-Glucosidase Active For Oligomaltosaccharides and α-Glucans", Biochemica et Biophysica Acta., 787, pp. 281-289 (1984).

Campbell, Jr., L. L., "Purification and Properties of an α-Amylase from Facultactive Thermophilic Bacteria", α-Amylase Studies, pp. 154-161.

Suzuki, Y. et al., "Production of Extracellular α--Glucosidase by a Thermophilic Bacillus Species", Applied and Environmental Microbiology, pp. 807-812 (1976).

Suzuki, Y. et al., "Purification and Properties of Extracellular α-Glucosidase of a Thermophile, Bacillus Thermoglucosidius KP 1006", Biochimica et Biophysica Acta., 445, pp. 386-397 (1976).

Suzuki, Y. et al., "Assignment of A -Nitrophenyl- -D--Glucopyranoside-Hydrolyzing-Glucosidase of Bacillus Stearothermophilus ATCC 12016 to an Exo-Oligo-1,6-Glucosidase", Biochemica et Biophysica Acta., 704, pp. 476-483 (1982).

Warth, A. D., "Stabilization of Spore Enzymes to Heat by Reduction in Water Activity", Sporulation and Germination, Proceedings of the Eighth International Spore Conference Woods Hole, Massachusetts, pp. 249-252 (1980).

Priest, F. G., "Extracellular Enzyme Synthesis in the Genus Bacillus", Bacteriological Reviews, pp. 711-753 (1977).

Hodges, N. A., "A Comparison of Heat Resistance in Commercially Available *Bacillus sterothermophilus* Spore Preparations Used for Monitoring Steam Sterilization", J. Pharm. Pharmacol., 34, pp. 259-260 (1982).

Starkey, D. H., "The Use of Indicators For Quality Control of Sterilizing Processes in Hospital Practice: A Review", American Journal of Infection Control, vol. 8, No. 3, pp. 79-84 (1980).

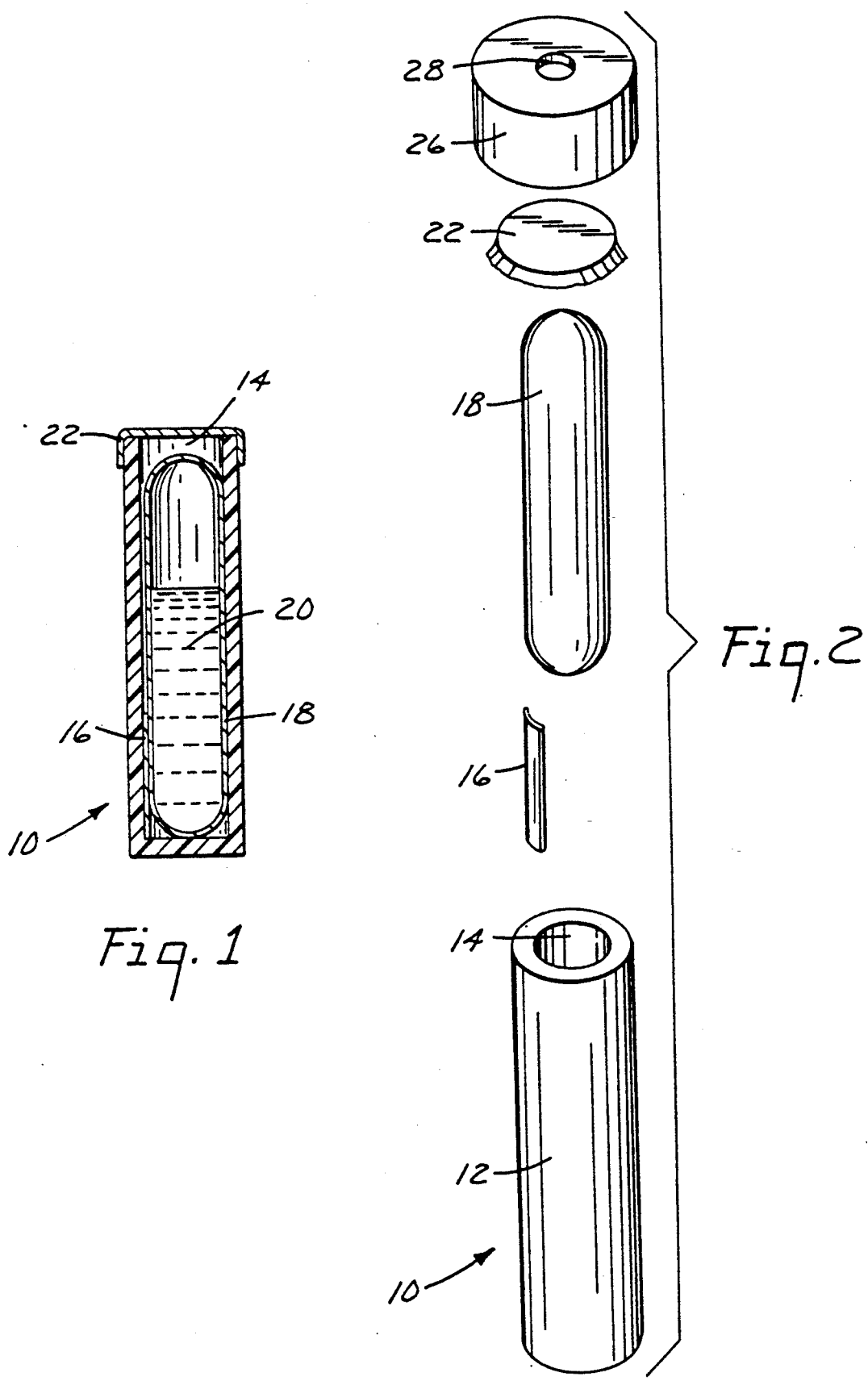

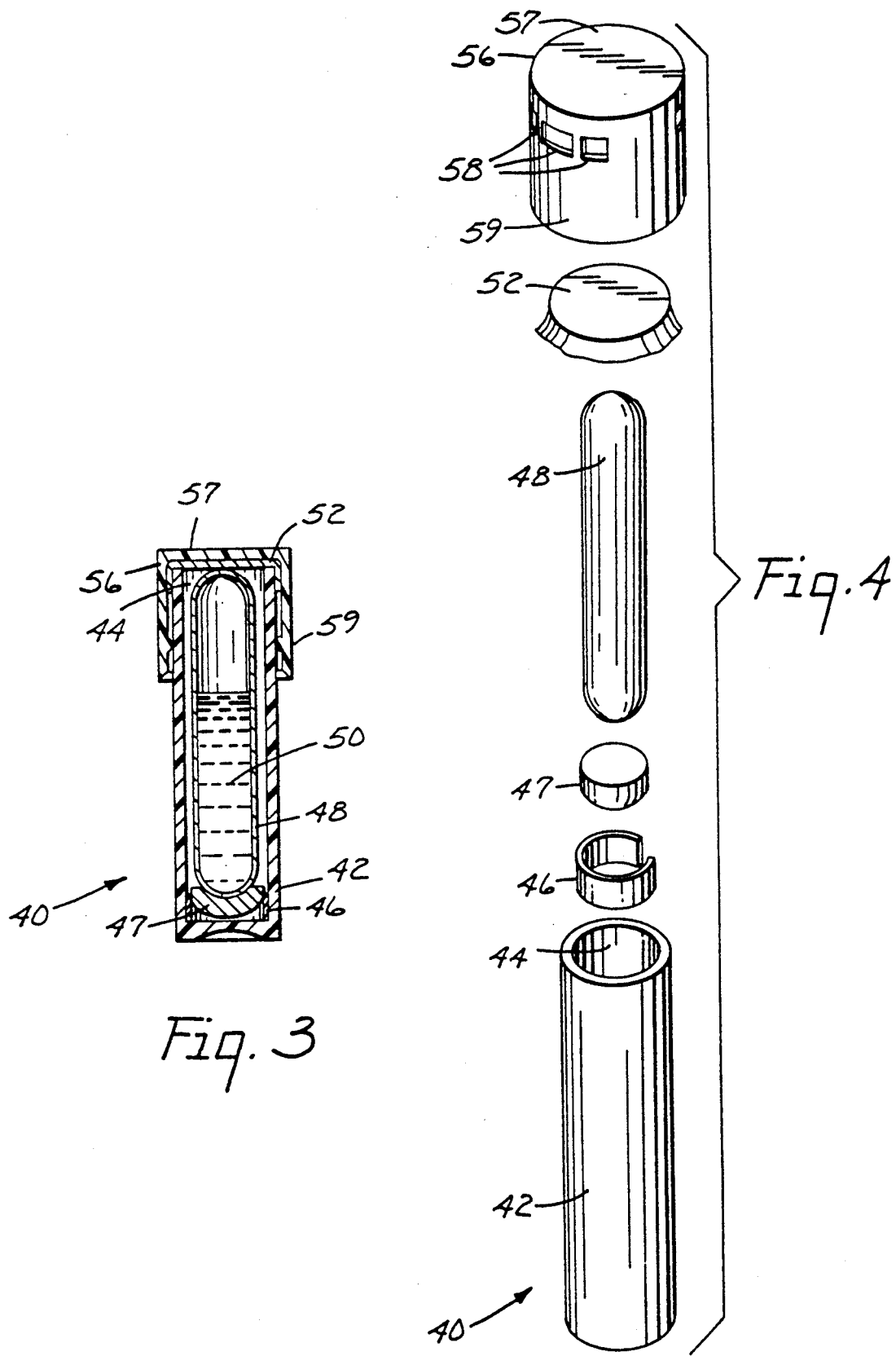

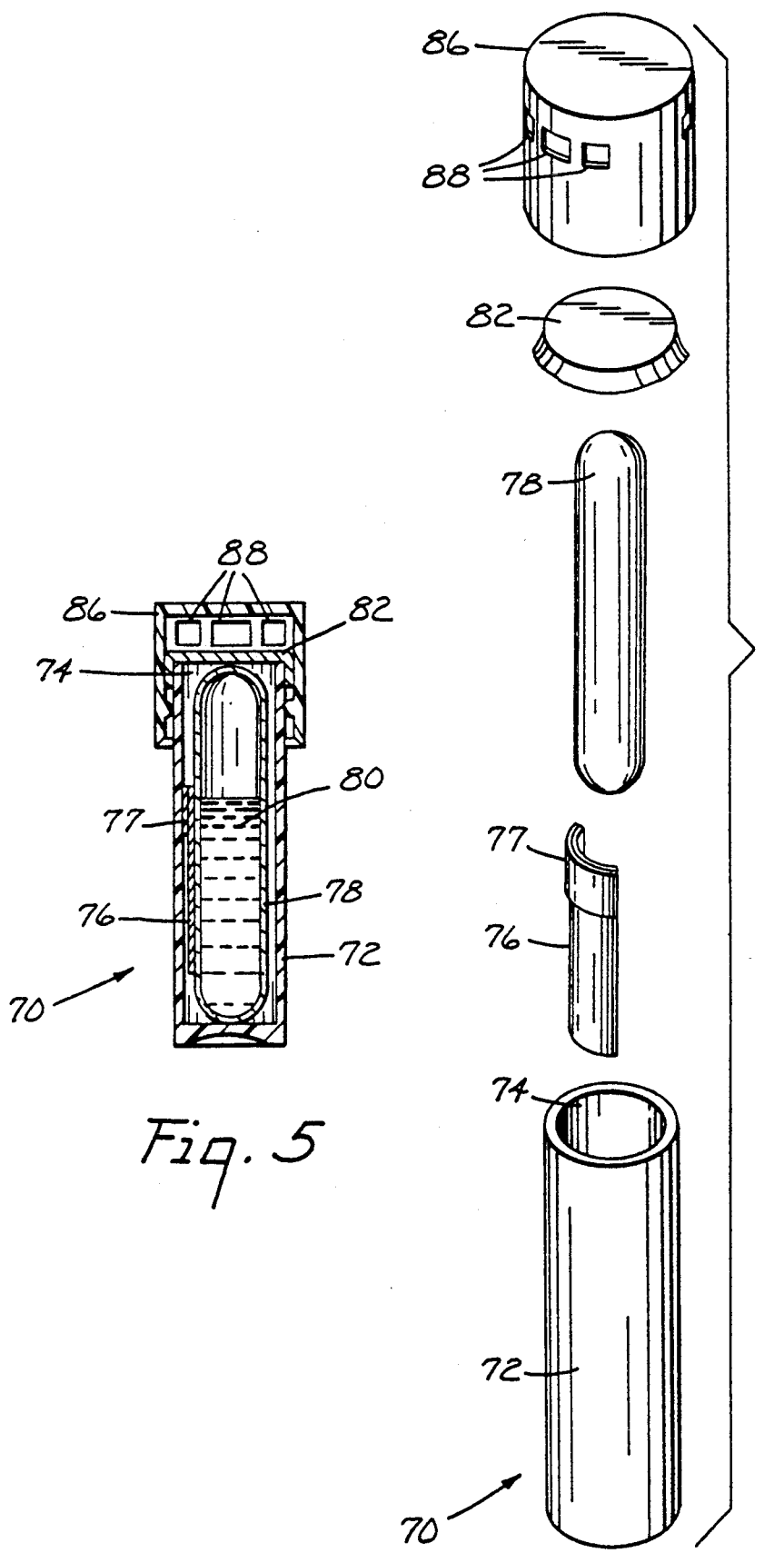

RAPID METHOD FOR DETERMINING EFFICACY OF A STERILIZATION CYCLE AND RAPID READ-OUT BIOLOGICAL INDICATOR

FIELD OF THE INVENTION

The present invention relates to a rapid method for determining the efficacy of a sterilization cycle. In particular, the present invention employs an enzyme whose activity can be correlated with the viability of at least one microorganism commonly used to monitor sterilization efficacy, hereinafter referred to as a "test microorganism". The enzyme, following a sterilization cycle which is sublethal to the test microorganism, remains sufficiently active to react with an enzyme substrate in a relatively short period of time, e.g., normally eight hours or less However, the enzyme is inactivated or appreciably reduced in activity following a sterilization cycle which is lethal to the test microorganism. The invention further relates to biological sterility indicators which include such an enzyme.

BACKGROUND OF THE INVENTION

Biological indicators and chemical indicators used to determine the efficacy of sterilization are well known in the art. In conventional biological indicators, a test organism which is many times more resistant to the sterilization process employed than most organisms which would be present by natural contamination, is coated on a carrier and placed in a sterilizer along with the articles to be sterilized. After completion of the sterilization cycle, the carrier is incubated in nutrient medium to determine whether any of the test organism survived the sterilization procedure. Growth of a detectable number of organisms normally takes a minimum of twenty-four hours. During this period, the supposedly sterilized articles should be quarantined.

In frequent practice, however, the hospital has neither the space for proper quarantining of the supposedly sterilized articles, nor a sufficient number of the articles themselves to permit actual quarantining. As a result, the supposedly sterilized articles are placed back into stock on the assumption that sterilization was proper and will be confirmed by a subsequent report from the laboratory.

Commercially available chemical indicators utilize chemicals which indicate sterility by color changes, or change from solid to liquid state. The advantage to such chemical indicators is that the results are known by the end of the sterilization cycle. However, those results indicate only, as in the device described in U.S. Pat. No. 4,448,548, that a particular temperature has been reached for a certain period of time; or, as in U.S. Pat. No, 4,348,209, that ethylene oxide gas was present. These devices do not indicate whether all conditions necessary to inactivate the test organism have been achieved. Only the living organism can sense the true relationships of physical and chemical parameters necessary to affect sterilization. Therefore, it is recognized in the art of sterilization that biological tests are the most accurate sterility tests.

There remains a need for a sterility indicator which will provide rapid results, yet provide a high level of confidence that all parameters, necessary to achieve sterilization, including the interrelated parameters of time, temperature and concentrations of moisture, chemicals or radiation dose, have been reached.

SUMMARY OF THE INVENTION

The present invention provides a method of determining the efficacy of a sterilization cycle, whether the sterilizing media be steam, dry heat, radiation, ethylene oxide, or other gaseous or liquid agents, which combines the reliability of the conventional biological indicators with a speed closer to that of the chemical indicators. The present invention provides methods and devices for indicating sterilization efficacy which, in most cases, can indicate sterilization failure within eight hours.

The method of the present invention comprises
 a) subjecting to a sterilization cycle a source of active enzyme, said enzyme having activity which correlates with the viability of at least one microorganism commonly used to monitor sterilization; and
 b) incubating the enzyme source, following the completion of the sterilization cycle, with an effective amount of a substrate system for that enzyme, which system is capable of reacting with any residual active enzyme to produce a detectable enzyme-modified product.

The reaction mixture is then evaluated in, e.g., a fluorometer or a colorimeter, to determine the presence of any enzyme-modified product. The existence of detectable enzyme-modified product above background within an established period of time (dependent upon the identity of the enzyme and the substrate, the concentration of each, and the incubation conditions) indicates a sterilization failure. The lack of detectable enzyme-modified product within the established period of time indicates a sterilization cycle which has been lethal to the test organism and is therefor adequate.

The source of active enzyme may be the purified enzyme isolated from an organism, or may be a microorganism, which may itself be one commonly used to monitor sterilization, such as *Bacillus stearothermophilus* or *Bacillus subtilis*. When such a microorganism is used as the enzyme source, the method of the present invention may include the step
 c) incubating any of the microorganisms which remain viable, following the completion of the sterilization cycle, with an aqueous nutrient medium capable, with incubation, of promoting growth of viable microorganisms, and a detector material capable of undergoing a detectable change in response to growth of the microorganisms, under conditions suitable to promote growth of viable microorganisms.

The present invention further provides rapid read-out sterility indicators useful in practicing the above-described methods. One such sterility indicator comprises:
 a) an outer container having liquid impermeable and substantially non-gas absorptive walls, the container having at least one opening therein, with a gas-transmissive, bacteria-impermeable means covering the opening; and
 b) contained within the outer container, a detectable amount of an isolated active enzyme whose activity correlates with the viability of at least one microorganism commonly used to monitor sterilization.

Another rapid-read out sterility indicator comprises:
 a) an outer container having liquid impermeable and substantially non-gas absorptive walls, the container having at least one opening therein, with a gas-transmissive, bacteria-impermeable means covering the opening;

b) contained within the outer container, a source of active enzyme in a detectable concentration, the enzyme having activity which correlates with the viability of at least one microorganism commonly used to monitor sterilization; and c) also contained within the outer container an effective amount of an enzyme substrate system capable of reacting with active enzyme to produce a detectable enzyme-modified product.

The ability of the present invention to rapidly determine the efficacy of a sterilization cycle is based upon the discovery that 1) certain enzymes remain active following a sterilization cycle which is marginally sufficient to kill the test microorganism whose viability correlates with the enzyme's activity; and 2) the enzyme activity following the marginal sterilization cycle is sufficient to convert a substrate system for that enzyme to a detectable concentration of product within a relatively short period of time, e.g., generally less than about eight hours.

Where a test microorganism is used along with, or as the source of, the enzyme, very low numbers of the test microorganism can survive the marginal sterilization cycle. However, there is sufficient enzyme activity associated with the inactivated microorganisms to indicate a sterilization failure.

The enzyme detection method of the present invention acts as a fail safe in marginal sterilization cycles because the enzymes of the present invention are more resistant to sterilization conditions than the test microorganism. In less complete sterilization cycles the existence of detectable enzyme-modified product, and, hence, the existence of enzyme activity can be used to predict the survival or viability of the test microorganism if it were subjected to the same sterilization conditions and incubated with nutrient medium for at least twenty-four hours.

BRIEF DESCRIPTION OF THE FIGURES

FIG. 1 is a cross-sectional view of one embodiment of a sterility indicator of the present invention, with the closure device 26 removed.

FIG. 2 is an exploded perspective view of the sterility indicator of FIG. 1, closure device 26 included.

FIG. 3 is a cross-sectional view of a preferred embodiment of an indicator of the present invention, with closure 56 in the closed position.

FIG. 4 is an exploded perspective view of the indicator of FIG. 3.

FIG. 5 is a cross-sectional view of another preferred embodiment of a sterility indicator of the present invention, with closure 86 in the open position.

FIG. 6 is an exploded perspective view of the sterility indicator of FIG. 5.

DETAILED DESCRIPTION OF THE INVENTION

Figure 7:
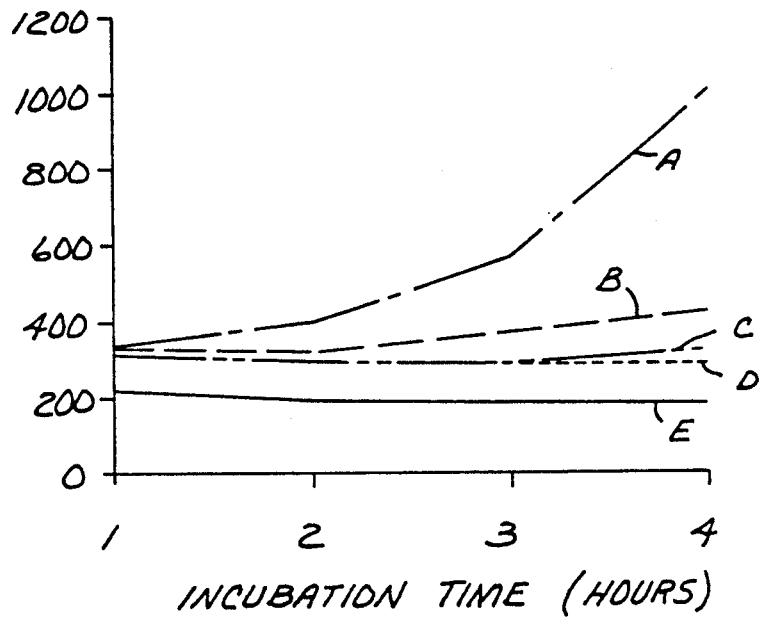
FIG. 7 is a graphic representation of relative fluorescence versus incubation time for sterility indicators of this invention, after exposure to a sterilization cycle for varying periods of time.

The enzymes useful in the practice of the present invention are enzymes including extracellular and intracellular enzymes, whose activity correlates with the viability of at least one microorganism commonly used to monitor sterilization efficacy, hereinafter referred to as a "test" microorganism. By "correlates" it is meant that the enzyme activity, over background, can be used to predict future growth of the test microorganism. The enzyme must be one which following a sterilization cycle which is sublethal to the test microorganism, remains sufficiently active to react with a substrate system for the enzyme, within twenty-four hours, and in preferred embodiments within eight hours or less, yet be inactivated or appreciably reduced in activity following a sterilization cycle which would be lethal to the test microorganism.

The following test has proven useful in identifying those enzymes having the requisite characteristics to be useful in the sterilization monitoring devices and methods of the present invention. The enzyme when subjected to sterilization conditions which would be just sufficient to decrease the population of $1 \times 10^6$ test microorganisms by about 6 logs (i.e., to a population of about zero as measured by lack of outgrowth of the test microorganisms), has residual enzyme activity which is equal to "background" as measured by reaction with a substrate system for the enzyme; however, the enzyme upon being subjected to sterilization conditions sufficient only to decrease the population of $1 \times 10^6$ test microorganisms by at least 1 log, but less than 6 logs, has enzyme activity greater than "background" as measured by reaction with the enzyme substrate system. The enzyme substrate system is a substance, or mixture of substances, which is acted upon by the enzyme to produce a detectable, e.g., fluorescent or colored, enzyme-modified product. The enzyme activity is measured by the amount of detectable enzyme-modified product produced. Preferably, the enzyme is one which has sufficient activity, following sterilization conditions insufficient to decrease the population of the test microorganism by 6 logs, to react with the enzyme substrate system and produce a detectable amount of enzyme-modified product within twenty-four hours, preferably within eight or less hours, and most preferably within two or less hours.

Preferably, the activity of the enzyme after sterilization conditions insufficient to decrease the microorganism population by 6 logs, is at least 2 percent greater, and more preferably at least 5 percent greater, than background, and most preferably is at least 10 percent above background. It is understood that the residual enzyme activity level which is defined as "background" for purposes of this invention, may be higher than that achieved by the spontaneous conversion of enzyme substrate to product after the enzyme has been totally and irreversibly inactivated.

Enzymes which have been found to meet the above-described test include hydrolytic enzymes from spore-forming microorganisms. Such enzymes include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, N-acetyl-$\beta$-glucosaminidase, beta-D-cellobiosidase, alanine aminopeptidase, proline aminopeptidase, tyrosine aminopeptidase, phenylalanine aminopeptidase, beta-D-glucuronidase, and a fatty acid esterase, derived from spore-forming microorganisms, such as *Candida, Bacillus* and *Clostridium* species of microorganisms.

Particularly useful enzymes from *Bacillus stearothermophilus* include alpha-D-glucosidase, beta-D-glucosidase, alkaline phosphatase, acid phosphatase, butyrate esterase, caprylate esterase lipase, leucine aminopeptidase, chymotrypsin, phosphohydrolase, alpha-D-galactosidase, beta-D-galactosidase, alanine aminopeptidase, tyrosine aminopeptidase, and phenylalanine aminopeptidase and a fatty acid esterase. Particularly useful enzymes from *Bacillus subtilis* include alpha-L-arabinofuranosidase, beta-D-glucosidase, N-acetyl-β-glucosaminidase, beta-D-cellobiosidase, alanine aminopeptidase, proline aminopeptidase, tyrosine aminopeptidase, leucine aminopeptidase and phenylalanine aminopeptidase.

Beta-D-glucosidase and alpha-L-arabinofuranosidase from *Bacillus subtilis* are particularly useful in the monitoring of ethylene oxide sterilization. Alpha-D-glucosidase from *Bacillus stearothermophilus* is particularly useful to monitor steam sterilization conditions.

The source of active enzyme may be:

1) the purified, isolated enzyme derived from an appropriate microorganism;

2) a microorganism to which the enzyme is indigenous or added by genetic engineering; or 3) a microorganism to which the enzyme has been added during sporulation or growth, such that the enzyme is incorporated or associated with the microorganism, e.g., an enzyme added to a spore during sporulation which becomes incorporated within the spore. Preferred microorganisms which may be utilized as the source of an enzyme useful in the practice of the present invention are bacteria or fungi in either the spore or vegetative state. Particularly preferred sources of enzyme include *Bacillus, Clostridium, Neurospora,* and *Candida* species of microorganisms.

When a microorganism is used as the source of active enzyme, the method of the present invention may include the step of incubating any of the microorganisms which remain viable, following the completion of the sterilization cycle, with an aqueous nutrient medium. Inclusion of this step confirms by conventional techniques whether the sterilization conditions had been sufficient to kill all of the microorganisms in the indicator, indicating that the sterilization conditions had been sufficient to sterilize all of the items in the sterilizer. If growth of the microorganism is used in a conventional manner to confirm the results of the enzyme test, the microorganism should be one which is conventionally used to monitor sterilization conditions. These conventionally used microorganisms are generally many times more resistant to the sterilization process being employed than most organisms encountered in natural contamination. The bacterial spore is recognized as the most resistant form of microbial life. It is the life form of choice in all tests for determining the sterilizing efficacy of devices, chemicals and processes. Spores from *Bacillus* and *Clostridia* species are the most commonly used to monitor sterilization processes utilizing saturated steam, dry heat, gamma irradiation and ethylene oxide.

Particularly preferred microorganisms commonly used to monitor sterilization conditions include *Bacillus stearothermophilus* and *Bacillus subtilis. Bacillus stearothermophilus* is particularly useful to monitor sterilization under steam sterilization conditions. The enzyme alpha-D-glucosidase has been identified in spores of *Bacillus stearothermophilus,* such as those commercially available as "ATCC 8005" and "ATCC 7953" from American Type Culture Collection, Rockville, MD *Bacillus subtilis* is particularly useful to monitor conditions of gas and dry heat sterilization. The enzyme beta-D-glucosidase has been found in *B.* subtilis (e.g., commercially available as "ATCC 9372" from American Type Culture Collection).

Alternatively, in the event that isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. Again, in such a case, the method of the present invention may include the step of incubating any viable microorganism remaining after the sterilization cycle with an aqueous nutrient medium to confirm the sterilization efficacy.

The present invention, although herein described primarily in terms of a single enzyme and/or microorganism species, should be understood to refer as well to the use of a plurality of enzymes and/or microorganism species. For example, a single sterility indicator may contain three types of isolated enzymes (which may be derived from three types of microorganisms), one enzyme being resistant to heat, a second being resistant to gaseous sterilizing media, and a third being resistant to radiation, e.g., gamma and beta irradiation. Similarly, a single sterility indicator may contain three species of microorganisms, one species being resistant to heat, a second species being resistant to gaseous sterilizing media, and the third species being resistant to radiation.

In the context of this application, an enzyme substrate system is by definition a substance or mixture of substances acted upon by an enzyme and converted into an enzyme-modified product. In general, the enzyme-modified product is a luminescent, fluorescent, colored or radioactive material. However, the enzyme substrate system can consist of a compound which when reacted with the enzyme, will yield a product which will react with an additional compound or composition to yield a luminescent, fluorescent, colored or radioactive material. Preferably, where the substrate system is to be included in the indicator device during sterilization, the substrate must not spontaneously break down or convert to a detectable product during sterilization or incubation. For example, in devices used to monitor steam and dry heat sterilization, the substrate must be stable at temperatures between about 20° and 180° C. Preferably also, where the enzyme substrate system is to be included with conventional growth media, it must be stable in the growth media, e.g., not auto fluoresce in the growth media.

The prior art includes a number of fluorogenic and chromogenic substrates for the detection of enzymes of diverse origin which are known, commercially available, and have been used in a variety of enzymatic procedures. (M. Roth, *Methods of Biochemical Analysis,* Vol. 17, D. Block, Ed., Interscience Publishers, New York, 1969, p. 189; S. Udenfriend, *Fluorescence Assay in Biology and Medicine,* Academic Press, New York, 1962, p. 312; and D. J. R. Lawrence, "Fluorescence Techniques for the Enzymologist", *Methods in Enzymology,* Vol. 4, S. P. Colowick and N. O. Kaplan, Eds., Academic Press, New York, 1957, p. 174, incorporated herein by reference.) There are two basic types of enzyme substrate systems described for the detection of specific enzymes. The first type of substrate system can be either fluorogenic or chromogenic, and can be given a chemical formula such as, AB. When acted upon by the enzyme, AB, breaks down to A+B. B, for example, would be either fluorescent or colored. A specific example of a fluorogenic substrate of this type would be 4-methylumbelliferyl phosphate. In the presence of the enzyme phosphatase, the substrate will be broken down into 4-methylumbelliferone and phosphate. Other fluorogenic substrates of this type include the derivatives of 4-methylumbelliferyl, 7-amido-4-methylcoumarin, indoxyl and fluorescein, listed below. An example of a chromogenic substrate of this type is 5-bromo-4-chloro-3-indolyl phosphate. In the presence of phosphatase, the substrate will be broken down into indigo blue and phosphate. Other chromogenic substrates of this type include derivatives of 5-bromo-4-chloro-3-indolyl, nitrophenol and phenolphtalein, listed below.

The second type of substrate system commonly used for the detection of enzymes can be given the chemical formula CD, for example, which will be converted by a specific enzyme to C+D. However, neither C nor D will be fluorescent or colored, but D is capable of being further reacted with compound Z to give a fluorescent or colored compound, thus indicating enzyme activity. A specific fluorogenic example of this type is the amino acid lysine. In the presence of the enzyme lysine decarboxylase, lysine loses a molecule of $CO_2$. The remaining part of the lysine is then called cadaverine, which is strongly basic. A basic indicator such as 4-methylumbelliferone can be incorporated and will fluoresce in the presence of a strong base. A chromogenic substrate of this type would be 2-naphthyl phosphate. The enzyme phosphatase, reacts with the substrate to yield $\beta$-naphthol. The liberated $\beta$-naphthol reacts with a chromogenic reagent containing 1-diazo-4-benzoylamino-2,5-diethoxybenzene, commercially available as "Fast Blue BB Salt" from Sigma Chemical, to produce a violet color. Other examples of this type are listed under the naphthyl derivatives below.

Thus, from the foregoing one can readily appreciate that it is possible to determine the presence of specific enzymes in microorganisms through a variety of approaches.

A preferred enzyme substrate system is a fluorogenic one, defined herein as a compound capable of being enzymatically modified, e.g., by hydrolysis, to give a derivative fluorophor which has an appreciably modified or increased fluorescence.

It is understood that the fluorogenic compounds are in themselves either non-fluorescent or meta-fluorescent (i.e., fluorescent in a distinctly different way e.g., either by color or intensity, than the corresponding enzyme-modified products) and appropriate wavelengths of excitation and detection, in a manner well known to users of fluorometric instrumentation, are used to separate the fluorescence signal developed by the enzyme modification from any other fluorescence that may be present.

The prior art includes a number of fluorogenic substrates for enzymes of diverse origin which are known, commercially available, and have been used in enzymological procedures. Among these are a variety of fluorogenic 4-methylumbelliferyl derivatives (hydrolysable to 4-methylumbelliferone); derivatives of 7-amido-4-methyl-yl-coumarin, e.g. GB Patent No. 1,547,747 and European Patent No. 0,000,063 (Ajinomoto), both patents incorporated herein by reference; diacetylfluorescein derivatives; and fluorescamine.

Useful 4-methylumbelliferyl derivatives include:
4-methylumbelliferyl-2-acetamido-4,
6-0-benzylidene-2-deoxy-$\beta$-D-glucopyranoside;
4-methylumbelliferyl acetate;
4-methylumbelliferyl-N-acetyl-$\beta$-D-galactosaminide;
4-methylumbelliferyl-N-acetyl-$\alpha$-D-glucosaminide;
4-methylumbelliferyl-N-acetyl-$\beta$-D-glucosaminide;
2'-(4-methylumbelliferyl)-$\alpha$-D-N-acetyl neuraminic acid;
4-methylumbelliferyl $\alpha$-L-arabinofuranoside;
4-methylumbelliferyl $\alpha$-L-arabinoside;
4-methylumbelliferyl butyrate;
4-methylumbelliferyl $\beta$-D-cellobioside;
methylumbelliferyl $\beta$-D-N, N'-diacetyl chitobioside;
4-methylumbelliferyl elaidate;
4-methylumbelliferyl $\beta$-D-fucoside;
4-methylumbelliferyl $\alpha$-L-fucoside;
4-methylumbelliferyl $\beta$-L-fucoside;
4-methylumbelliferyl $\alpha$-D-galactoside;
4-methylumbelliferyl $\beta$-D-galactoside;
4-methylumbelliferyl $\alpha$-D-glucoside;
4-methylumbelliferyl $\beta$-D-glucoside;
4-methylumbelliferyl $\beta$-D-glucuronide;
4-methylumbelliferyl p-guanidinobenzoate;
4-methylumbelliferyl heptanoate;
4-methylumbelliferyl $\alpha$-D-mannopyranoside;
4-methylumbelliferyl $\beta$-D-mannopyranoside;
4-methylumbelliferyl oleate;
4-methylumbelliferyl palmitate;
4-methylumbelliferyl phosphate;
4-methylumbelliferyl propionate;
4-methylumbelliferyl stearate;
4-methylumbelliferyl sulfate;
4-methylumbelliferyl $\beta$-D-N N',N"-triacetylchitotriose;
4'-methylumbelliferyl 2,3,5-tri-o-benzoyl-$\alpha$-L-arabinofuranoside;
4-methylumbelliferyl-p-trimethylammonium cinnamate chloride;
and 4-methylumbelliferyl $\beta$-D-xyloside.

Useful 7-amido-4-methylcoumarin derivatives include:
L-alanine-7-amido-4-methylcoumarin;
L-proline-7-amido-4-methylcoumarin;
L-tyrosine-7-amido-4-methylcoumarin;
L-leucine-7-amido-4-methylcoumarin;
L-phenylalanine-7-amido-4-methylcoumarin; and
7-glutarylphenylalanine-7-amido-4-methylcoumarin.

Useful peptide derivatives of 7-amido-4-methyl coumarin include: N-t-BOC-11e-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Useful diacetyfluorescein derivatives include fluorescein diacetate, fluorescein di-($\beta$-D-galactopyranoside), and fluorescein dilaurate.

Where the enzyme whose activity is to be detected is alpha-D-glucosidase, chymotrypsin, or fatty acid esterase, e.g., from *Bacillus stearothermophilus*, the fluorogenic enzyme substrate is most preferably 4-methylumbelliferyl-alpha-D-glucoside, 7-glutarylphenylalanine- 7-amido-4-methyl coumarin, or 4-methylumbelliferyl heptanoate, respectively. Where the enzyme whose activity is to be detected is alpha-L-arabinofuranosidase, e.g., derived from *Bacillus subtilis*, a most preferred fluorogenic enzyme substrate is 4-methylumbelliferyl-alpha-L-arabinofuranoside. Where the enzyme whose activity is to be detected is beta-D-glucosidase, e.g., derived from *Bacillus subtilis*, a most preferred fluorogenic enzyme substrate is 4-methylumbelliferyl-beta-D-glucoside.

Another useful enzyme substrate system is a chromogenic compound capable of being enzymatically modified to give a derivative chromophor, or a product which reacts with another compound to give a derivative chromophor, which chromophor has a different or more intense color. It is understood that the chromogenic compounds are in themselves either non-colored or colored in a distinctly different way, e.g., either by color or intensity, than the corresponding enzyme-modified products. Appropriate wavelengths of excitation and detection, in manners well known to users of colorometric instrumentation are used to separate the colored signal developed by the enzyme modification from any other color that may be present.

A number of chromogenic substrates have been used in enzymological procedures. Among the useful chromogenic substrates are 5-bromo-4-chloro-3-indolyl derivatives; nitrophenyl derivatives; indoxyl derivatives; and phenolphtalein derivatives.

Useful 5-bromo-4-chloro-3-indolyl derivatives include 5-bromo-6-chloro-3-indolyl acetate, 5-bromo-4-chloro-3-indolyl acetate, 5-bromo-4-chloro-3-indoxyl-β-D-galactopyranoside, 5-bromo-4-chloro-3-indolyl-1,3-diacetate, 5-bromo-4-chloro-3-indolyl-β-D-fucopyranoside, 5-bromo-4-chloro-3-indolyl-β-D-glucopyranoside, 5-bromo-4-chloro-3-indolyl-β-D-glucuronic acid, 5-bromo-4-chloro-3-indolyl phosphate, and 5-bromo-4-chloro-3-indolyl sulfate.

Useful nitrophenyl derivatives include p-nitrophenol and o-nitrophenol derivatives. Particularly useful p-nitrophenols include diethyl-p-nitrophenyl phosphate; di-p-nitrophenyl phosphate; p-nitrophenyl-2-acetamido-2-deoxy-3-O-β-galactopyranosyl-β-glucopyranoside; p-nitrophenyl-2-acetamido-2-deoxy-β-glucopyranoside; p-nitrophenyl acetate; p-nitrophenyl-N-acetyl-β-D-glucosaminide; p-nitrophenyl-β-D-N,N'-diacetylchitobioside; p-nitrophenyl-α-glucopyranoside; p-nitrophenyl-α-maltoside; p-nitrophenyl-β-maltoside; p-nitrophenyl-α-mannopyranoside; p-nitrophenyl-β-mannopyranoside; p-nitrophenyl myristate; p-nitrophenyl palmitate; p-nitrophenyl phosphate; bis(p-nitrophenyl)phosphate; tris(p-nitrophenyl)phosphate; p-nitrophenyl-β-glucopyranoside; p-nitrophenyl-β-glucuronide; α-p-nitrophenylglycerine; p-nitrophenyl-α-rhamnopyranoside; p-nitrophenyl stearate; p-nitrophenyl sulfate; p-nitrophenyl-2,3,4,6-tetra-O-acetyl-β-glucosaminide; p-nitrophenyl thymidine monophosphate; p-nitrophenyl-2,3,4-tri-O-acetyl-β-glucuronic acid methyl ester; and p-nitrophenyl valerate.

Particularly useful o-nitrophenols include o-nitrophenyl acetate, o-nitrophenyl-β-glucoside and o-nitrophenyl-β-D-glucopyranoside. Other particularly useful nitrophenyl derivatives include nitrophenyl-β-fucopyranoside; nitrophenyl-α-galactopyranoside; nitrophenyl-β-galactopyranoside; nitrophenyl butyrate; nitrophenyl caprate; nitrophenyl caproate; nitrophenyl caprylate; nitrophenyl laurate; and nitrophenyl propionate.

Useful indoxyl derivatives include indoxyl-acetate; indoxyl β-D-glucoside; 3-indoxyl sulfate; 3-indoxyl phosphate.

Useful phenolphtalein derivatives include: phenolphthalein dibutyrate; phenolphthalein diphosphate; phenolphthalein disulfate; phenolphthalein glucuronic acid; phenolphthalein mono-β-glucosiduronic acid; phenolphthalein mono-β-glucuronic acid; and phenolphthalein mono-phosphate.

All of the above-described chromogenic substrates will react directly with an appropriate enzyme to produce a chromophor.

Additional enzyme substrates containing 1-naphthyl, 2-naphthyl and Napthyl-AS-BI derivatives are usefully employed if the derivative enzyme modified product is further reacted with a chromogenic reagent, such as diazotized dyes, e.g., 1-diazo-4-benzoylamino-2, 5-diethoxybenzene, (commercially available as "Fast Blue BB Salt" from Sigma Chemical), 1-diazo-4-benzoylamino-2, 5-diethoxybenzene, p-diazo-2,5-diethoxy-N-benzoyalanine, 4-chloro-2-methylbenzene diazonium chloride, and o-aminoazotoluene diazonium salt, to produce a chromophor.

Particularly useful 1-napthyl derivatives include 1-naphthyl-N-acetyl-β-D-glucosaminide.

Particularly useful 2-naphthyl derivatives include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-α-D-galactopyranoside; 2-naphthyl-βD-galacto-pyranoside; 2-naphthyl-2-D-glucopyranoside; 6-bromo-2-naphthol-β-D-glucopyranoside; 6-bromo-2-naphthyl-2-D-mannopyranoside; and 2-naphthyl-α-L-fucopyranoside.

Particularly useful naphthyl-AS-BI derivatives include naphthyl-AS-BI-phosphate; and naphthyl-AS-BI-β-D-glucuronide.

Where the enzyme whose activity is to be detected is alpha-D-glucosidase, e.g., from *Bacillus stearothermophilus*, the chromogenic enzyme substrate is most preferably p-nitrophenyl-α-glucopyranoside. Where the enzyme whose activity is to be detected is alpha-L-arabinofuranosidase, e.g., derived from *Bacillus subtilis*, a most preferred chromogenic enzyme substrate is p-nitrophenyl-alpha-L-arabinofuranoside. Where the enzyme whose activity is to be detected is beta-D-glucosidase, e.g., derived from *Bacillus subtilis*, a most preferred chromogenic enzyme substrate is p-nitrophenyl-β-D-glucopyranoside.

In order to carry out the method of the present invention, it is essential that the operator be knowledgable concerning the enzyme whose activity is to be detected, and the enzyme substrates which will react with the enzyme so as to produce a product which can be detected either by its fluorescence, color, etc. (See M. Roth, *Methods of Biochemical Analysis*, Vol. 7, D. Glock, Ed., Interscience Publishers, New York, N.Y., 1969, incorporated herein by reference.) The appropriate enzyme substrate to be utilized will depend upon the identity of the enzyme whose activity is under study. Below is a list of a number of preferred fluorogenic and colorogenic enzyme substrates and an enzyme which will react with the substrate to produce a product having appreciably modified or increased fluorescence or color.

| Substrate | Enzyme Probed |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbellifery-β-D-galactopyranoside | β-D-Galactosidase |
| 4-Methylumbelliferyl-α-D-galactopoyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate diNa salt | Alkaline Phosphatase |
| Phenolphthalein dibutyrate | Esterase |
| Phenolphthalein diphosphate | Acid or Alkaline phosphatase |
| Phenolphthalein diphosphate pentaNa salt | Acid and Alkaline phosphatase |
| Phenolphthalein-β-D-glucuronide Na salt | β-D-Glucuronidase |
| Phenolphthalein-β -D-glucuronide | β-D-Glucuronidase |
| L-Phenylalanine ethylester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium -glycerophosphate | Acid or Alkaline phosphatase |
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide | Leucine aminopeptidase |
| L-Valyl-2-naphthylamide | Valine aminopeptidase |
| N-glutaryl-phenylalanine-2-naphthylamine | Chymotrypsin |
| Naphthyl-AS-BI-phosphate | Phosphohydralase |
| Indoxyl acetate | Lipase |
| N-Methylindoxyl acetate | Lipase |
| N-Methylindoxyl myristate | Lipase |
| 5-Bromoindoxyl acetate | Lipase |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-β-D-glucuronic acid | β-D-Glucuronidase |
| Diacetylfluorescein | Lipase/esterase |

The enzyme and its appropriate enzyme substrate are reacted in a buffered aqueous solution. The ionic conditions of the buffered solution should be such that the enzyme and enzyme substrate are not effected. Preferably, an isotonic buffer, such as phosphate buffered saline solution, tris(hydroxymethyl) aminomethane-HCl solution, or acetate buffer is chosen. These preferred isotonic buffers are compatible with most fluorogenic and chromogenic enzyme substrates. Another consideration in choosing the buffers is its influence on the enzyme activity. For example, phosphate buffered saline contains a high concentration of inorganic phosphate which is a strong competitive inhibitor of alkaline phosphatase. For this enzyme, a Tris-HCl buffer is, therefore, advised.

The concentration of enzyme substrate present in the reaction mixture is dependent upon the identity of the particular substrate and enzyme, the amount of enzyme-product that must be generated to be detectable, either visually or by instrument, and the amount of time that one is willing to wait in order to determine whether active enzyme is present in the reaction mixture. Preferably, the amount of enzyme substrate is sufficient to react with any residual active enzyme present, after the sterilization cycle, within about an eight hour period of time, such that at least $1 \times 10^{-8}$ molar enzyme-modified product is produced. Where the enzyme substrate is a 4-methylumbelliferyl derivative, it has been found that its concentration in the aqueous buffered solution is preferably between about $1 \times 10^{-5}$ and $1 \times 10^{-3}$ molar.

The aqueous solution containing the enzyme substrate also preferably is adjusted to a pH of about 5.0 to 9.5, preferably about 7.5, in order to prevent autofluorescence of some basic fluorogenic substrates.

The enzyme substrate in the aqueous buffered solution is incubated with the enzyme source whose activity is to be detected after the enzyme source has been subjected to the sterilization cycle. Incubation is continued for a period of time and under conditions sufficient to liberate a detectable amount of the enzyme modified product, assuming that any of the enzyme remains active. In general, the amount of product which is detectable by known methods is at least $1 \times 10^{-8}$ molar. Preferably, the incubation conditions are sufficient to generate at least $1 \times 10^{-8}$ molar of enzyme-modified product, more preferably, about $1 \times 10^{-6}$ to $1 \times 10^{-5}$ molar of enzyme-modified product. The incubation time and temperature needed to produce a detectable amount of enzyme-modified product will depend upon the identity of the enzyme and the substrate, and the concentrations of each present in the reaction mixture. In general, the incubation time required is between about 1 minute and 12 hours, and the incubation is between about 20° and 70° C. Preferably, where *Bacillus subtilis* or *Bacillus stearothermophilus* is the source of the enzyme, the incubation time required is between about 10 minutes and 3 hours, and the incubation temperature required is between about 30° and 40° C., and between about 52° and 65° C., respectively.

Generally applicable methods for detecting enzyme modified product that may be used in biochemical analysis include photometric, potentiometric, gravimetric, calorimetric, conductometric, and amperometric techniques. For the purpose of this invention, fluorometric and spectrophotometric methods of measuring detectable enzyme modified product are preferred. For example, the specific enzyme substrate may comprise a 4-methylumbelliferyl derivative which on interaction with the enzyme gives rise to umbelliferone which is monitored fluorimetrically, or the substrate may comprise a nitrophenol, or similar type of derivative, which on interaction with the enzyme gives rise to a colored product which is monitored colorimetrically.

The procedure of the invention permits very rapid detection of enzyme activity, which can be used to predict conditions permitting survival of microorganisms and, thus, sterilization efficacy. The enzyme determination tests used generally require only a relatively short period of incubation, e.g., from about ten minutes up to about three hours, usually from about 30 to about 90 minutes to provide sufficient enzyme modified product for detection, e.g., by spectroscopic measurements.

In its simplest form, a sterility indicator useful in practicing the method of the present invention includes a source of active enzyme in a container having liquid impermeable and substantially gas non-absorptive walls. The container has at least one opening, to permit sterilizing media to come in contact with the enzyme and a gas-transmissive, bacteria-impermeable means covering the opening. Optionally, the indicator may include within the container:

1) a microorganism commonly used to monitor sterilization efficacy, either as the source of the enzyme or in addition to the source of the enzyme;

2) a carrier upon which is coated the source of active enzyme, alone or in combination with a sterilization resistant microorganism;

3) a substrate for the active enzyme and an aqueous reaction medium for the enzyme and it substrate; and 4) In the event that a sterilization resistant microorganism is utilized, nutrient growth media and a growth indicator. Sterility indicators similar to those described in U.S. Pat. Nos. 3,346,464; 3,585,112; 3,846,242; 4,291,122; 4,461,837; 4,416,984; 4,596,773; 3,440,144; 4,528,268; 2,854,384; 3,239,429; 3,752,743; 4,304,869; 4,579,823; and 4,580,682 may be usefully employed if an enzyme useful in the practice of the present invention is included in place of, or in addition to, the sterility resistant microorganism.

The following description is directed to Applicants' preferred embodiments. Many variations of the following devices are possible which will nonetheless fall within the scope of the present invention.

Referring now to FIGS. 1 and 2, a preferred sterility indicator is shown having an outer container in the shape of cylindrical tube 10, having substantially gas non-absorptive and liquid impermeable walls 12 and an open end 14. Tube 10 contains an enzyme carrier 16, such as a strip of filter paper, bearing a predetermined amount of active isolated enzyme and/or a predetermined number of viable microorganisms. Tube 10 also includes a normally sealed, pressure-openable inner container 18, such as a frangible glass ampoule, containing a suitable enzyme substrate dissolved or suspended in an aqueous buffered solution 20, and optionally including an aqueous nutrient growth medium. Preferably, the enzyme substrate is stable at temperatures between about 20° and 180° C. and is capable of reacting with active enzyme to yield a luminescent, fluorescent, colored or radioactive material. The aqueous nutrient medium is capable, with incubation, of promoting growth of viable microorganisms when contacted therewith. The inner container 18 is preferably snuggly retained within the outer container 10 so that very little of the volume of the outer container remains unoccupied. The glass ampoule 18 is separated from the wall 12 of the tube 10 by the filter paper carrier 16. The open end 14 of the tube 10 is provided with a gas-transmissive, bacteria-impermeable closure member 22, such as a sheet. The sheet 22 may be sealed to the open end 14 of the tube 10 by, e.g., heat or adhesive sealing, or by means of a closure device 26, such as a cap, (shown removed in FIG. 1) which has an aperture 28 therethrough. During sterilization with a gaseous sterilization agent, the gaseous sterilant permeates the sheet 22 and passes through the interior of the outer container to contact the enzyme carrier 16.

As shown in FIG. 2, the apparatus of FIG. 1 may be easily assembled by sequentially inserting into the open end 14 of the tube 10 the active enzyme carrier 16 and the flangible glass ampoule 18, and sealing the open end 14 of the tube with the sheet 22 by placing sheet 22 over open end 14 and then placing cap 26 over sheet 22, in closing engagement with tube 10.

Outer container 10 is made from material which will withstand the high temperatures encountered in steam sterilizers. Conventional steam sterilizers generally reach temperatures on the order of 121° C.–135° C. Additionally, the walls of container 10 must be substantially impermeable to gases and liquids. Outer container 10 which contains the carrier 16 which is coated with viable microorganisms or active isolated enzyme, and in which the residual active enzyme reacts with the enzyme substrate contained in pressure-openable inner container 18, is preferably translucent (including "transparent") so that a change in fluorescence or color may be visually observed without disassembling the indicator device. Preferably, also, the outer container 10 is sufficiently deformable so that the pressure-openable inner compartment 18 is ruptured when the outer compartment 10 is deformed, by using external pressure. Container 10 can be made by injection molding or extruding suitable materials, including polycarbonate, polypropylene, polyamides, polymethylpentenes and various polyesters. Polypropylene is the preferred material. These materials are sufficiently temperature resistant to withstand steam or dry heat sterilization cycles, non-absorbent of gaseous sterilizing media, liquid-impermeable, translucent or transparent and deformable.

The closure device 26 can be made from any material that will withstand the sterilization temperatures. As in the case of the container 10, suitable materials include polycarbonate, polypropylene, polyamides, polymethylpentenes and various polyesters, with polypropylene being preferred.

The active isolated enzymes and/or the microorganisms which are employed in the present invention normally are carried on a suitable carrier 16. It is contemplated, however, that the enzyme and/or microorganism may be carried by the inner walls of the outer container 10, or the outer walls of the inner container 18. Preferably, however, the isolated enzyme and/or microorganism are carried by the same or separate enzyme carriers. The enzyme carrier preferably is water-absorbent, such as filter paper, and should not inhibit microorganism growth or enzyme activity. Sheet-like materials such as cloth, nonwoven polypropylene, rayon or nylon, and microporous polymeric materials are especially preferred. However, metal foil substrates, for example, aluminum or stainless steel may be used, as well as substrates of glass (e.g., glass beads or glass fibers), porcelain, or plastic. Additionally, the enzyme carrier can be constructed of a combination of materials such as paper secured to a plastic or glass backing strip.

To assure reproducibility, it is desired that outer container 10 contain a predetermined amount of active enzyme. This is readily accomplished with isolated enzyme by using general methods of protein purification, such as salt fractionation, chromotography and electrophoresis as described in Colowick, S., and Kaplan, N.O. (Eds), *Methods in Enzymology*, Academic Press, New York, Vols. I-VII, (1957-1964), incorporated herein by reference. Preferably the initial concentration of isolated enzyme is between about $1 \times 10^{-10}$ and $5 \times 10^{-2}$ units, more preferably between about $1 \times 10^{-8}$ and $5 \times 10^{-3}$ units of enzyme, and most preferably between about $1 \times 10^{-7}$ and $1 \times 10^{-3}$ units. Where a microorganism is utilized, it is likewise desirable to use a predetermined approximate number of microorganisms. This is accomplished with bacterial or fungal spores by preparing a spore suspension having a known volumetric spore concentration, moistening the carrier 16 (e.g., filter paper) with a small, predetermined volume of the suspension, and drying the carrier. This method permits the approximate number of spores contained on the carrier to be easily calculated. Other methods, of course, may also be employed. Where the microorganism is utilized as the source of the enzyme, the microorganism population which should be used will depend on the activity of the enzyme in that organism. The enzyme activity is dependent upon the culture conditions and strain selection of the microorganism, but can be regulated by adjusting the microorganism population. Where the microorganism is *Bacillus stearothermophilus* or *Bacillus subtilis* the number of microorganisms necessary to produce sufficient enzyme is provided by about $1 \times 10^8$ to $1 \times 10^2$ microorganisms. Where the source of enzyme is *B. stearothermophilus*, about $1 \times 10^3$ to $1 \times 10^7$ microorganisms is preferred. Where *B. subtilis* is the source of the enzyme, about $1 \times 10^6$ to $1 \times 10^8$ microorganisms is preferred.

When a microorganism is used as the source of active enzyme, the incubation of the device can be continued after the time required to produce detectable enzyme-modified product, in order to confirm by conventional techniques whether the sterilization conditions had been sufficient to kill all of the microorganisms in the indicator, indicating that the sterilization conditions had been sufficient to sterilize all of the items in the sterilizer. If growth of the microorganism is used in a conventional manner to confirm the results of the enzyme test, the microorganism should be one which is conventionally used to monitor sterilization conditions. These conventionally used microorganisms are generally many times more resistant to the sterilization process being employed than most organisms encountered in natural contamination. Preferred microorganisms include *Bacillis stearothermophilus* and *Bacillus subtilis*.

Alternatively, in the event that isolated enzyme is utilized, or the microorganism used as the source of active enzyme is not more resistant to the sterilization conditions than the natural contaminants, another microorganism commonly used to monitor sterilization conditions can be included with container 10. In such a device, the isolated enzyme, or the microorganism from which a useful enzyme maybe derived, is used to obtain a reading of enzyme activity within generally about 10 minutes to 3 hours after incubation, and the commonly used microorganism is further incubated in nutrient media for at least about 24 hours to confirm the enzyme activity results.

An aqueous solution of the appropriate enzyme substrate is normally included in pressure-openable inner container 18. However, it is contemplated that the enzyme substrate in dry form could be included in outer container 10 along with enzyme carrier 16. In fact, the active enzyme and its substrate could be present in dry form in the same carrier 16. In this construction, inner container 18 would preferably carry the aqueous reaction medium necessary for the active enzyme and its substrate to react.

Preferably, when a microorganism commonly used to monitor sterilization is included in the device (either as the source of the active enzyme, or in addition to the source of active enzyme) and confirmation of microorganism survival by conventional methods is desired, inner container 18 contains an aqueous solution of the enzyme substrate and nutrient growth media. Preferably, the nutrient growth media is compatible with most fluorogenic and chromogenic enzyme substrates and is not a competitive inhibitor for the enzyme. The types of nutrient media usefully employed in the present invention are widely known to the art. Examples of preferred nutrient media are aqueous solutions of soybean-casein digest broth, fluid thioglycollate and Dextrose Tryptone (Difco Laboratories, Inc.) A modified tryptic soy broth base, without glucose, is especially preferred. To avoid contamination, such aqueous nutrient media normally is sterilized after having been placed in the inner compartment. Commonly known microbial growth indicators, which change color in the presence of viable microorganisms, are preferably present in at least one of the containers. The growth indicator material preferably is soluble in, and imparts color (upon microorganism growth) to, the aqueous nutrient medium so that a change in color may be easily observed through the translucent walls of the outer container. In addition, the growth indicator material is preferably selected so that it will not interfere with the color or luminescence of the enzyme-modified product. Growth indicator materials which may be employed in the present invention are well known to the art and include pH-sensitive dye indicators (such as bromthymol blue, brom cresol purple, phenol red, etc.), oxidation-reduction dye indicators (such as methylene blue, etc.). Such materials commonly undergo changes in color in response to a phenomenon of microorganism growth, such as changes in pH, oxidation-reduction potentials, etc.

The inner container 18 which contains the aqueous solution of enzyme substrate and/or which contains the aqueous nutrient medium, is of material which is impermeable to gases and liquids and is capable of being opened upon the application of pressure thereto (i.e., "pressure openable") to permit the enzyme substrate and/or nutrient medium to enter the outer container. The inner container is preferably of frangible material, such as glass, and, as mentioned above, is preferably snugly carried within the outer container in coacting relationship therewith to permit breakage or crushing of the inner container when the outer container is deformed. In another embodiment, the inner container may be sealed with a plug such that the plug is expelled to release the contents of the inner container upon application of pressure. In still another embodiment, the closure 26 may include an ampoule crushing device, as shown in U.S. Pat. No. 4,304,869, wherein the closure has tabs depending from the bottom of the closure device which upon depression of the closure device serve to crush the ampoule. Similarly, the device of the present invention may be used in a system having an ampoule crushing pin disposed in the bottom of the outer container 10.

The active enzyme-containing outer container 10 has at least one opening therein to permit the sterilant (e.g., steam, ethylene oxide) to contact the source of active enzyme during sterilization. This opening is normally closed or plugged with a gas-transmissive, bacteria-impermeable means. Suitable means include closure member 22, made of fibrous materials such as cotton, glass wool, cloth, nonwoven webs made from polypropylene, rayon, polypropylene/rayon, nylon, glass or other fibers, filter papers, microporous hydrophobic and hydrophilic films, open celled polymeric foams, and semi-permeable plastic films such as those described in U.S. Pat. No. 3,346,464. Fibrous or cellular materials are preferred because of the ease with which such materials transmit sterilizing gases. Preferred closure member materials include hydrophobic materials such as nylon web, microporous hydrophobic film, or glass fiber nonwoven web. Especially preferred is a microporous hydrophobic film, commercially available from Celanese Separations Products, Charlotte, NC, under the trade name "Celgar- ® K-442 Microporous Film". In effect, the fibrous or cellular closure members serve as filters for bacteria and fungi and hence should have pore sizes no larger than about 0.5 microns (e.g., be capable of preventing the passage therethrough of particles having dimensions larger than about 0.5 microns). Alternatively, the closure means may be a tortuous pathway that is bacteria-impermeable, such as that described in U.S. Pat. No. 4,461,837, incorporated herein by reference, and in commonly assigned copending U.S. Pat. No. 4883,641, issued Nov. 28, 1989.

A preferred embodiment of a sterilization indicator of the present invention is illustrated in FIGS. 3 and 4. The device includes an outer container 40, having substantially gas non-absorptive and liquid impermeable walls 42 and an open end 44. The outer container 40 includes a pressure-openable inner container 48 which contains an aqueous solution 50 of a suitable enzyme substrate, preferably in admixture with an aqueous nutrient medium. The open end 44 of the outer container 40 is covered by a gas-transmissive, bacteria-impermeable closure member 52. With that, the similarity between the device depicted in FIG. 1 ends. In the device of FIGS. 3 and 4, the enzyme carrier 46 is located at the bottom closed end of the outer container 40, and a barrier 47 is positioned like a plug between the enzyme carrier 46 and the pressure-openable inner container 48. The barrier 47 is preferably made of materials which are non-fluorescent, for use with fluorogenic enzyme substrates, such as nonwoven webs made from fibers such as cotton, rayon, polypropylene, polypropylene/rayon blends, nylon or glass. Most preferably barrier 47 is constructed from a polypropylene nonwoven web, such as "Thinsulate ® 200-B brand Thermal Insulation", commercially available from 3M, St. Paul, MN.

Barrier 47 serves to isolate the enzyme carrier 46 from the inner container 48, thus eliminating cold spots where the ampoule 48 may be positioned over the carrier 46. The existence of cold spots can cause condensation to collect on the enzyme carrier. The condensate may effect the activity of the enzyme contained on the carrier 46. Barrier 47 is preferably made from a hydrophobic material so that enzyme-modified product concentrates around the enzyme carrier and does not diffuse rapidly into the area of the container which is on the other side of the barrier. Maintaining a higher concentration of the enzyme-modified product in the lower portion of the indicator enables the enzyme modified product, whether it be luminescent or colored to be detected after a shorter period of incubation than would be the case if the carrier 46 was reacted with the entire contents of inner container 48. In general, as illustrated in Example 1, preferred devices which incorporate a barrier 47, provide reliable information on sterilization efficacy within about 10 minutes. Similar devices, not utilizing such a barrier, require about two hours to provide reliable sterilization efficacy information.

The closure 56 is comprised of a top 57 and depending sidewalls 59. The closure has a hollow body open at the bottom, with the interior diameter of the closure being about equal to the exterior diameter of outer container 40, so that closure 56 may be frictionally engaged over the open end 44 of outer container 40. Cut within the sidewalls 59 are preferably a plurality of windows 58. When the indicator device is placed in a load to be sterilized, the closure 56 is placed over the opening in the outer container in such a manner that the exterior sidewalls 42 of the outer container do not block windows 58. In such a position, sterilant in the sterilizer may enter container 40 by flowing through windows 58. Upon completion of the sterilization cycle, the closure may be fully inserted by depressing it to force the sidewalls 42 of the outer container into engagement with the interior surface of top 57 thereby blocking windows 58. The interior of the container 40 is then sealed from the outside environment.

FIGS. 5 and 6 illustrate an alternative preferred embodiment of the sterilization indicator of the present invention. The device includes, as does the device of FIGS. 3 and 4, an outer container 70, with gas non-absorptive and liquid impermeable walls 72 and an open end 74; a pressure-openable inner container 78 within outer container 70 containing an aqueous solution of enzyme substrate 80, preferably in admixture with nutrient growth medium; and gas-transmissive, bacteria-impermeable closure member 82, which is held over the open end 74 of the outer container by cap 86. The enzyme carrier 77 within outer container 70 is attached to a wick strip 76 by, for example, adhesive or heat sealing. The wick strip can be made from any water-absorbent material, such as filter paper, cloth, or rayon. Additionally, the wick strip can be constructed of a combination of materials such as paper secured to a plastic or glass backing strip. Preferably wick strip 76 is prepared from polyethylene coated paper. Preferably, the dimensions of the wick strip and the placement of the enzyme carrier on the wick strip are such that when the inner-container is ruptured the liquid therein is contained within the lower portion of the outer container and below the enzyme carrier 77. The aqueous enzyme substrate solution 80 travels up the wick strip 76 to enzyme carrier 77.

The enzyme-modified product concentrates on the enzyme carrier 77 and its presence is detected in a shorter period of time than would be the case if the carrier was exposed to the entire solution present in the inner container 78.

In use, the sterility indicator depicted in FIGS. 3 and 4 is placed in a sterilizer chamber together with a number of items to be sterilized by, for example, steam or ethylene oxide gas. When the indicator is in the sterilizer, the closure 56 is in the open position, such that windows 58 are open permitting entry of the sterilant. When the sterilizing agent is introduced into the chamber, the sterilant permeates through the closure member 52 and passes barrier 47 to inactivate the enzyme and kill the test microorganisms present on carrier 46. At the end of the sterilization cycle, the sterilant is replaced with filtered air. The sterility indicator is withdrawn from the sterilizer, the closure 56 is fully inserted to block windows 58, and glass ampoule 48 is broken by, for example, finger pressure, causing the aqueous solution of enzyme substrate and nutrient growth media to contact the enzyme carrier 46. The indicator is then placed in a suitable incubating environment (e.g. the indicator may be incubated at about 56° C. for about 10 minutes to 2 hours). Any enzyme not inactivated by the sterilant will react with its substrate, producing a preferably colored or fluorescent enzyme-modified product. The occurrence of a change in color or fluorescence is observed or measured spectrophotometrically through the translucent walls 42 of the outer container 40, and indicates that the sterilization cycle had not inactivated all the active enzyme on the carrier 46. The presence of active enzyme predicts survival and eventual outgrowth of the test microorganism and indicates that the sterilization cycle was perhaps insufficient to completely sterilize the items in the sterilizer. The absence of any change in color or fluorescence indicates that the sterilization cycle had been sufficient to inactivate all of the enzyme on the carrier 46, and hence was sufficient to sterilize the items in the sterilizer. With further incubation of the device (at 56° C. for about 24 to 48 hours) the early prediction of test microorganism survival can be confirmed by the existence color changes in the growth media.

A preferred method of monitoring the fluorescence of an indicator of this invention is a fluorimeter designed specifically for the devices described in this invention. A fluorimeter eliminates the subjective interpretation encountered when attempting to visually differentiate between low levels of fluorescent product and background or no fluorescence. A fluorimeter can be calibrated to detect a minimum amount of fluorescent product within a given incubation period.

A particularly preferred fluorimeter, designed for use with the devices of this invention, consists of a chamber designed to block ambient light while positioning the outer container of the indicator such that the enzyme carrier within can be illuminated with a 365 nm wavelength ultraviolet light, and a photodiode can detect any resultant fluorescence in the 460 nm wavelength region. The fluorimeter is calibrated to detect at least $1.0 \times 10^{-5}$ M 4-methylumbelliferone.

Several methods can be used to differentiate the fluorescent positive devices from the non-fluorescent or negative devices. In the first approach, a fluorescent threshold limit equivalent to the fluorescence produced by $1 \times 10^{-5}$ M 4-methylumbelliferone is established in the fluorimeter. When a test sample with sufficient active enzyme converts enough substrate to exceed the threshold limit, after the enzyme carrier is allowed to react with the substrate at e.g., 56° C. for 15 minutes, the fluorimeter indicates a positive sample by illuminating, for example, a red light. If the fluorescent product produced by reaction of the enzyme and its substrate does not exceed the threshold limit, after the 15 minute incubation, for example, the fluorimeter will indicate a negative or non-fluorescent sample, with, for example, a green light.

In the second approach, the fluorimeter measures the initial fluorescence, at the beginning of the incubation period. The fluorimeter chamber is heated to the optimum temperature for the specific enzyme being tested in the device. In the case of the enzyme alpha-D-glucosidase derived from *Bacillus stearothermophilus*, the temperature is 56° C. During the incubation period, the fluorimeter continues to monitor the fluorescence and will indicate a positive fluorescent sample when at least a 5% increase in intensity above the initial fluorescence is detected, by, for example, a red light. If less than a 5% increase occurs within the established incubation time, the fluorimeter will indicate a negative or non-fluorescent sample by, for example, activating a green light.

The sterility indicator of the present invention has been described primarily with reference to sterilizing media such as ethylene oxide, steam and the like. The indicator is not, however, limited to these uses, and may as well be used to indicate the efficacy of other sterilizing media, such as dry heat, radiation, propylene oxide, methyl bromide, ozone, chlorine dioxide, formaldehyde, and other gaseous and liquid agents.

The invention will be illustrated by the following non-limiting examples, in which all percentages are percent by weight, unless otherwise indicated.

EXAMPLE 1

This example illustrates the correlation between the fluorescent results of the enzymatic detection method of the present invention, and the results of conventional spore survival methods of detection. This example also illustrates the shorter read-out times which can be achieved with the device illustrated in FIGS. 3 and 4, which utilizes a barrier 47 between the ampoule 48 and the enzyme carrier 46.

*Bacillus stearothermophilus* commercially available as "ATCC 7953" from American Type Culture Collection, Rockville, MD, was grown overnight (16 hours) at 58° C. in tryptic soy broth. This culture was used to inoculate the surface of agar plates consisting of 8 g/l nutrient broth, 4 g/l yeast extract, 0.1 g/l manganese chloride and 20 g/l agar at pH 7.2. Plates were incubated at 58° C. for 72 hours. Spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. This cleaning procedure was repeated several times. The *Bacillus stearothermophilus* spores were coated on 6.35 mm (¼ inch) in diameter filter paper discs, commercially available as "S&S #903 Grade Filter Paper" from Schleicher & Schuell, Inc., Keene, NH, at a population of $1.6 \times 10^6$ spores per disc. This was accomplished by preparing a suspension of the *B. stearothermophilus* spores in water at a concentration of $1 \times 10^8$ spore/ml, pipetting 10 μl of this suspension on each filter paper disc and allowing the discs to dry.

Two types of devices were constructed as follows.

ple to yellow, was determined visually after 24 hours of incubation at 56° C.

The results are reported in Table I.

TABLE I

| Device | Exposure Time (minutes) | FLUORESCENCE Incubation Time (Minutes) at 56° C. Number Positives/5 Tested | | | | | | | Spore Growth at 24 hr. |
|---|---|---|---|---|---|---|---|---|---|
| | | 10 | 20 | 30 | 60 | 120 | 180 | 240 | |
| 1 | 0.5 | 5 | 5 | 5 | 5 | 5 | 5 | 5 | 5 |
| (Spore Strip | 1.0 | 5 | 5 | 5 | 5 | 5 | 5 | 5 | 5 |
| on Bottom | 1.5 | 5 | 5 | 5 | 5 | 5 | 5 | 5 | 5 |
| with Barrier | 2.0 | 3 | 3 | 3 | 3 | 3 | 3 | 3 | 3 |
| Material) | 2.5 | 0 | 0 | 0 | 0 | 2* | 2* | 3* | 0 |
| | 3.0 | 0 | 0 | 0 | 0 | 0 | 0 | 0 | 0 |
| 2 | 0.5 | 0 | 0 | 0 | 5 | 5 | 5 | 5 | 5 |
| (Spore Strip | 1.0 | 0 | 0 | 0 | 5 | 5 | 5 | 5 | 5 |
| on Bottom | 1.5 | 0 | 0 | 0 | 5 | 5 | 5 | 5 | 5 |
| without | 2.0 | 0 | 0 | 0 | 5 | 5 | 5 | 5 | 5 |
| Barrier | 2.5 | 0 | 0 | 0 | 0 | 3* | 3* | 3* | 1 |
| Material) | 3.0 | 0 | 0 | 0 | 0 | 0 | 0 | 0 | 0 |

*Indicates one or more false positive reactions which appear to be the result of residual enzyme activity following spore inactivation in marginal sterilization cycles The first device was constructed as illustrated in FIGS. 3 and 4, with the spore coated strip 46 on the bottom of the outer compartment 40 and a barrier 47 between the enzyme substrate-containing ampoule 48 and the spore strip. A 1.75 mm (11/16 inch) diameter disc of polypropylene blown microfiber material, with a weight of 200 g/sq. meter, commercially available as "Thinsulate ® 200-B brand Thermal Insulation" from 3M, St. Paul, MN, was used as the barrier 47. The ampoule 48 contained 0.67 ml nutrient medium, consisting of 17 g of a bacteriological peptone and 0.17 g of L-alanine, as well as 0.1 g 4-methylumbelliferyl-alpha-D-glucoside, commercially available from Sigma Chemical Company, St. Louis, MO., dissolved in 200 μl of N, N-dimethylformamide, and 0.03 g bromocresol purple pH indicator dye, per liter of water. The pH of the enzyme substrate and nutrient medium solution was adjusted to 7.6 with 0.1 N sodium hydroxide.

The outer vial 40 the cap 56 are both made from polypropylene. The outer vial was 5.08 cm (2.0 inches) long, with an outer diameter of 85.1 mm (0.335 inches) and an internal diameter of 77.0 mm (0.303 inches). The cap was 1.275 cm (0.510 inch) long with an internal diameter of 83.3 mm (0.328 inch). The inner ampoule 48 was made of glass and was 3.96 cm (1.56 inches) long, with an outer diameter of 65.5 mm (0.258 inches) and a wall thickness of 2.5 mm (0.010 inches). The closure member 52 was a 1.27 mm (½ inch) in diameter piece of polypropylene, commercially available as "Celgard ® K-442 Microporous Film", from Celanese Separations Products, Charlotte, N.C.

The second device was identical to the first device, except that the barrier 47 was omitted.

Five unit batches of both types of devices were placed in metal instrument trays and exposed at 132° C. in a gravity displacement steam sterilizer, commercially available as an "Amsco Eagle ™ Model 2013 Sterilizer", from American Sterilizer Company, Erie, PA., for 0.5, 1.0, 1.5, 2.0,. 2.5 and 3.0 minutes. After exposure the inner ampoules containing the enzyme substrate and nutrient medium were crushed and the units were incubated at 56° C. An ultraviolet light ($\lambda = 366$ nm) was used to illuminate the vials for visually read fluorescence after 10 min., 20 min., 30 min., 60 min., 120 min., 180 min., and 240 minutes of incubation. Additionally, spore growth, as indicated by a color change from pur- The data in Table I illustrates that the presence of active alpha-D-glucosidase can be detected by the methods of the present invention much more quickly than can the detection of viable spores. The data illustrates that the detection of active enzyme in a device can be used to predict eventual spore growth in the device.

The data in Table I illustrates that using device 1 (with a barrier between the ampoule and the spore strip) enzyme activity can be detected after 10 minutes for all units which show spore growth after 24 hours of incubation. Using device 2 (without barrier material), 2 hours of incubation is required in order to detect enzyme activity in all units which show spore growth after 24 hours of incubation.

EXAMPLE 2

Devices were constructed as illustrated in FIGS. 5 and 6, with the enzyme carrier 77 on a wick 76. One spore strip, prepared in accordance with Example 1, was heat sealed to one end of a 0.10 mm thick polyethylene coated paper, 6.35 mm × 28.58 mm. The ampoule 78 contained 5 ml/l of a nonionic surfactant, commercially available as "Tween ™ 80 Polyoxyethylene Sorbitan Monooleate", from ICI Americas, Inc., Wilmington, Delaware, to aid in the wetting of the spore carrier, as well as the enzyme substrate, nutrients and indicators present in the solution of Example 1. The outer vial, cap and inner ampoule were identical to those used in the devices of Example 1. The closure member was a sterilization grade filter paper.

Five unit batches of devices were placed in metal instrument trays and exposed at 132° C. in a gravity displacement steam sterilizer, commercially available as an "Amsco Eagle ™ Model 2013 Sterilizer", from American Sterilizer Company, Erie, PA., for 0.5, 1.0, 1.5, 2.0,. 2.5 and 3.0 minutes. After exposure the inner ampoules were crushed and the devices were incubated at 56° C. An ultraviolet light ($\lambda = 366$ nm) was used to illuminate the vials for visually read fluorescence after 10 min., 20 min., 30 min., 60 min., 120 min., 180 min., and 240 minutes of incubation. Additionally, spore growth, as indicated by a color change from purple to yellow, was determined visually after 24 hours of incubation.

The results are reported in Table II.

TABLE II

| Exposure Time (minutes) | FLUORESCENCE Incubation Time (Minutes) at 56° C. Number Positive/5 Tested | | | | | | | 24 hr. Growth |
|---|---|---|---|---|---|---|---|---|
| | 10 | 20 | 30 | 60 | 120 | 180 | 240 | |
| 0.5 | 5 | 5 | 5 | 5 | 5 | 5 | 5 | 5 |
| 1.0 | 5 | 5 | 5 | 5 | 5 | 5 | 5 | 5 |
| 1.5 | 5 | 5 | 5 | 5 | 5 | 5 | 5 | 5 |
| 2.0 | 0 | 0 | 0 | 0 | 4* | 5* | 5* | 0 |
| 2.5 | 0 | 0 | 0 | 0 | 0 | 0 | 0 | 0 |
| 3.0 | 0 | 0 | 0 | 0 | 0 | 0 | 0 | 0 |

*Indicates one or more false positive reactions which appear to be the result of residual enzyme activity following spore inactivation in marginal sterilization cycles The data in Table II illustrates that much quicker detection of spore survival can be achieved using the devices and enzyme detection methods of the present invention in contrast to standard 24 hour spore growth.

EXAMPLE 3

This example illustrates several enzymes, associated with *Bacillus stearothermophilus*, which are useful in the practice of the present invention. In this example an enzyme substrate kit, commercially available as "API-XYM TM System" from API Analytab Products, Plainview, NY, was utilized. This kit consists of 19 different dehydrated, chromogenic enzymatic substrates, packed individually in a series of microcupules. The addition of an aqueous sample to each microcupule rehydrates the substrate. The test kit is incubated for a desired interval and the reactions are visualized after the addition of the detector reagents supplied with the system.

Devices made according to Device 1 of Example 1, were exposed for 1 minute or 3 minutes at 132° C. in the steam sterilizer used in Example 1. It was determined that the *Bacillus stearothermophilus* spores when used in this device will survive a one-minute exposure and be killed after 3 minutes. After exposure the spore strips were aseptically transferred to each microcupule in the enzyme substrate kit and 50 μl of sterile distilled water was added to each well. One kit contained the spore strips exposed for 1 minute, a second kit contained the spore strips exposed for 3 minutes and a third kit contained unexposed spore strips.

The kit containing the unexposed strips was incubated at 56° C. for 5 hours. The kits containing exposed spore strips were allowed to incubate at 56° C. for 7 hours. After incubation, the detector reagents A and B (available with the "API-XYM TM System") were added for color development of any enzymatic reactions occurring in the microcupules of each kit.

The detection of color in each microcupule of each kit is reported in Table III. A number of the enzymes showed readily detectable activity after 1 minute exposure, and no or substantially decreased activity after 3 minutes exposure. Several of the enzymes were not indigenous to *B. stearothermophilus* and did not illustrate detectable activity in the unexposed state. Several other enzymes (including myristate lipase, valine aminopeptidase, chymotrypsin, and beta-glucuronidase) which did not illustrate detectable activity in the unexposed state, apparently were activated by the exposure to heat. It is believed that these enzymes which show detectable activity after a 1 minute exposure and no activity or reduced activity after 3 minutes exposure, could be usefully employed in the present invention, even if no enzyme activity is detected in the unexposed state.

TABLE III

| Enzyme Assayed For | Spore Strip Exposure | | |
|---|---|---|---|
| | Unexposed | 1 Minute | 3 Minute |
| Negative control | — | — | — |
| Alkaline phosphatase | +2 | +3 | — |
| Butyrate esterase | +4 | +5 | — |
| Caprylate esterase lipase | +2 | +3 | — |
| Myristate lipase | — | VW | — |
| Leucine aminopeptidase | +1 | +5 | — |
| Valine aminopeptidase | — | VW | — |
| Cystine aminopeptidase | — | — | — |
| Trypsin | — | — | — |
| Chymotrypsin | — | +4 | — |
| Acid phosphatase | +3 | +4 | +1 |
| Phosphohydrolase | +4 | +5 | +3 |
| Alpha-galactosidase | +5 | +5 | — |
| Beta-galactosidase | — | — | — |
| Beta-glucuronidase | — | VW | — |
| Alpha-glucosidase | +5 | +5 | — |
| Beta-glucosidase | +4 | VW | — |
| N-acetyl-beta-glucosaminidase | — | — | — |
| Alpha-mannosidase | — | — | — |
| Alpha-fucosidase | — | — | — |

— = No color development
VW = Very weak color development
+1 = Weak color development
+2, 3, 4 = Intermediate color development
 (color development increasing with increasing number)
+5 = Strong color development Table III illustrates that a number of enzymes present in *B. stearothermophilus*, including alkaline phosphate, butyrate esterase, caprylate esterase lipase, myristate lipase, leucine aminopeptidase, valine aminopeptidase, chymotrypsin, acid phosphatase, phosphohydrolase, alpha-galactosidase, beta-glucuronidase, and alpha-glucosidase, B-glucosidase, have sufficient activity following a sublethal sterilization exposure to be detected before growth of the spore is detected.

EXAMPLE 4

*Bacillus stearothermophilus* spores, prepared in accordance with Example 1, were coated and dried on 6.35×28.58 mm (¼×1⅛ inch) carriers made of a filter paper, commercially available as "S&S #591A Grade Filter Paper" from Schleicher and Schuell, Inc. of Keene, NH. at concentrations of $1.0 \times 10^7$, $7.5 \times 10^5$, $1.0 \times 10^5$, $1.7 \times 10^4$, $2.8 \times 10^3$ spores per carrier. Devices were assembled using these spore strips, as shown in FIGS. 3 and 4 and described as Device 1 in Example 1.

Three unit batches of devices were placed in metal instrument trays and exposed at 132° C. in a gravity displacement steam sterilizer, commercially available as an "Amsco Eagle TM Model 2013 Steam Sterilizer", from American Sterilizer Company, Erie, PA., for 1.0, 1.5, 2.0,. 2.5 and 3.0 minutes. After exposure the inner ampoules were crushed and the devices were incubated at 56° C. An ultraviolet light ($\lambda = 366$ nm) was used to illuminate the vials to visually detect fluorescence after 10 min., 20 min., 30 min., 60 min., 120 min., 180 min., 240 min., 300 min. and 360 minutes of incubation. Additionally, spore growth, as indicated by a color change from purple to yellow, was determined visually after 24 hours of incubation.

The results are reported in Table IV.

TABLE IV

| Spore Population | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 15 | 30 | 45 | 60 | 120 | 180 | 240 | 300 | 360 | |
| $1.0 \times 10^7$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 1* | 1* | 1* | 2* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $7.5 \times 10^5$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 2* | 2* | 2* | 2* | 2* | 2* | 2* | 2* | 2* | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $1.0 \times 10^5$ | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 1* | 1* | 1* | 1* | 1* | 1* | 1* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $1.7 \times 10^4$ | 1.0 | 0 | 0 | 2 | 2 | 3 | 3 | 3 | 3 | 3 | 3 |
| | 1.5 | 0 | 0 | 3* | 3* | 3* | 3* | 3* | 3* | 3* | 2 |
| | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| $2.8 \times 10^3$ | 1.0 | 0 | 0 | 0 | 0 | 0 | 3 | 3 | 3 | 3 | 3 |
| | 1.5 | 0 | 0 | 0 | 0 | 0 | 0 | 0 | 0 | 0 | 0 |
| | 2.0 | 0 | 0 | 0 | 0 | 0 | 0 | 0 | 0 | 0 | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates one or more false positives which appears to be the result of residual enzyme activity following spore inactivation in marginal sterilization cycles Table IV illustrates that even with a low spore population, the spore survivors were predicted by enzyme activity (i.e., fluorescence) well before any growth of the organism was detected.

EXAMPLE 5

This example compares read-out times for devices employing different strains of *Bacillus stearothermophilus* spores. The following strains were tested: "ATCC 8005", commercially available from American Type Culture Collection, Rockville, MD; spores obtained from growing the microorganism contained in three different commercially available biological indicators, "ATTEST TM Biological Indicator", 3M, St. Paul, MN, "Proof PLUS TM Biological/Chemical Indicator", American Sterilizer Co., Erie, PA, and "Assert TM Biological/Chemical Indicator ", Surgicot, Smithville, NY; "NCTC 10003" commercially available from Nation Collection of Type Cultures, Colindale, London, England; "German Earthspore" obtained by culturing earth strips supplied by the Hygiene Institute of Hamburg, Hamburg, Germany, in tryptic soy broth after exposure at 121° C. for 5 minutes (the 5 min. exposure was used to kill all the vegetative organisms present in the earth so only *B. stearothermophilus* remains; and Scandinavian strain isolated from spore strips produced by Statens Institute for Falkehelse, Oslo, Norway.

All spores were grown on a nutrient agar medium as described in Example 1. The spores were centrifuged at 11,000 rpm for 5 hours at 4° C. in density gradient commercially available as Percoll ® from Pharmacia Fine-Chemicals AB, Uppsala, Sweden. After centrifuging the spores were resuspended in sterile distilled water. With the German Earthspore, two distinct layers of cells were isolated in the density gradient during centrifugation. Using phase contact microscopy, the bottom layer was found to be predominantly spores and the top layer was predominantly vegetative cells and vegetative debris with a small number of spores. Both layers were tested separately.

The spores were coated and dried on 6.35×28.58 mm (¼×⅛ inch) strips of filter paper ("S&S 591A Grade Filter Paper") at a population of at least $1 \times 10^6$ per carrier. Devices were assembled as in Device 1, Example 1, except that in one batch of devices using the "ATCC 8005" spores, the enzyme substrate used was 4-methylumbelliferyl-beta-D-galactoside, commercially available from Sigma, 0.1 g/l dissolved in 200 μl N, N-dimethylformamide, instead of 4-methylumbelliferyl-alpha-D-glucoside, in order to detect the enzyme activity of beta-D-galactosidase on the "ATCC 8005" spores. Three unit batches were exposed at 132° C. for 1.0, 1.5, 2.0, 2.5 and 3.0 minutes in an "Amsco Eagle TM Model 2013 Steam Sterilizer". After exposure the inner ampoules were crushed and the units were incubated at 56° C. An ultraviolet light ($\lambda=366$ nm) was used to illuminate the vials for visually read fluorescence after 10 min., 20 min., 30 min., 60 min., 120 min., 180 min., and 240 minutes of incubation. Additionally, spore growth, as indicated by a color change from purple to yellow, was determined visually after 24 hours of incubation.

The results are reported in Table V.

TABLE V

| Strain | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 10 | 20 | 30 | 40 | 50 | 60 | 120 | 180 | 240 | |
| "ATCC 8005" | 1.0 | 3 | 3 | 3 | 3 | 3 | 3 | 3 | 3 | 3 | 3 |
| (enzyme substrate- | 1.5 | 0 | 1 | 1 | 1 | 1 | 1 | 2 | 2 | 2 | 3 |

TABLE V-continued

| Strain | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 10 | 20 | 30 | 40 | 50 | 60 | 120 | 180 | 240 | |
| 4-methylumbelliferyl- | 2.0 | 0 | 0 | 0 | 0 | 0 | 0 | 0 | 0 | 0 | 0 |
| α-D-glucoside) | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "ATCC 8005" | 1.0 | 3 | 3 | 3 | 3 | 3 | 3 | 3 | 3 | 3 | 3 |
| (enzyme substrate- | 1.5 | 0 | 2 | 3 | 3 | 3 | 3 | 3 | 3 | 3 | 3 |
| 4-methylumbelliferyl- | 2.0 | 0 | 0 | 0 | 0 | 0 | 0 | 0 | 0 | 0 | 0 |
| β-D-galactoside) | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "PROOF PLUS TM | 1.0 | 3 | 3 | 3 | 3 | 3 | 3 | 3 | 3 | 3 | 3 |
| Biological/Chemical | 1.5 | 3 | 3 | 3 | 3 | 3 | 3 | 3 | 3 | 3 | 3 |
| Indicator" | 2.0 | 1 | 3 | 3 | 3 | 3 | 3 | 3 | 3 | 3 | 3 |
| | 2.5 | 0 | 0 | 0 | 2 | 3 | 3 | 3 | 3 | 3 | 3 |
| | 3.0 | 0 | 0 | 0 | 0 | 0 | 0 | 0 | 0 | 0 | 0 |
| "ATTEST TM | 1.0 | 3 | 3 | 3 | 3 | 3 | 3 | 3 | 3 | 3 | 3 |
| Biological | 1.5 | 3 | 3 | 3 | 3 | 3 | 3 | 3 | 3 | 3 | 3 |
| Indicator" | 2.0 | 3 | 3 | 3 | 3 | 3 | 3 | 3 | 3 | 3 | 3 |
| | 2.5 | 0 | 0 | 0 | 0 | 3 | 3 | 3 | 3 | 3 | 3 |
| | 3.0 | 0 | 0 | 0 | 0 | 0 | 0 | 0 | 0 | 0 | 0 |
| "ASSERT TM | 1.0 | 3 | 3 | 3 | 3 | 3 | 3 | 3 | 3 | 3 | 3 |
| Biological/Chemical | 1.5 | 3 | 3 | 3 | 3 | 3 | 3 | 3 | 3 | 3 | 3 |
| Indicator" | 2.0 | 0 | 3 | 3 | 3 | 3 | 3 | 3 | 3 | 3 | 3 |
| | 2.5 | 0 | 0 | 0 | 0 | 1 | 1 | 3 | 3 | 3 | 3 |
| | 3.0 | 0 | 0 | 0 | 0 | 0 | 0 | 0 | 0 | 0 | 0 |
| "NCTC 10003" | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 3 | 3 | 3 | 3 | 3 | 3 | 3 | 3 | 3 | 3 |
| | 2.5 | 0 | 0 | 2 | 3 | 3 | 3 | 3 | 3 | 3 | 3 |
| | 3.0 | 0 | 0 | 0 | 0 | 0 | 0 | 0 | 0 | 0 | 0 |
| "German | 1.0 | 2 | 3 | 3 | 3 | 3 | 3 | 3 | 3 | 3 | 3 |
| Earthspore" | 1.5 | 0 | 2 | 3 | 3 | 3 | 3 | 3 | 3 | 3 | 3 |
| | 2.0 | 0 | 0 | 0 | 0 | 0 | 0 | 0 | 0 | 0 | 1 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| "German | 1.0 | 0 | 3 | 3 | 3 | 3 | 3 | 3 | 3 | 3 | 3 |
| Earthspore" | 1.5 | 0 | 0 | 0 | 1 | 3 | 3 | 3 | 3 | 3 | 2 |
| Vegatative + | 2.0 | 0 | 0 | 0 | 0 | 0 | 0 | 0 | 0 | 1 | 2 |
| Spores | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Scandinavian | 1.0 | 3 | 3 | 3 | 3 | 3 | 3 | 3 | 3 | 3 | 3 |
| strain | 1.5 | 3 | 3 | 3 | 3 | 3 | 3 | 3 | 3 | 3 | 3 |
| | 2.0 | 0 | 0 | 0 | 0 | 0 | 1* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates one or more false positive reactions which appear to be the result of residual enzyme activity following spore inactivation in marginal sterilization cycles Table V illustrates that all strains of *B. stearothermophilus* tested had enzyme activity (either alpha-D-glucosidase or beta-D-galactosidase) that correlated with spore survival. In most units where spores survived, fluorescence was detected within 2 hours of incubation and in many units fluorescence was detected after 10 minutes of incubation. The layer of cells consisting mostly of vegetative cells from the German Earthspore also had enzyme survival following the sublethal exposures. This indicates that the alpha-D-glucosidase associated with vegetative cells could be used in this invention. Several units with the Scandinavian strain had enzyme survival and no growth of the organism with further incubation. This has been observed previously and occurs in marginal cycles. The enzyme remains active slightly longer than the spore, and this provides an additional safety margin by monitoring more of the cycles insuring sterility of the items in the sterilizer.

EXAMPLE 6

*Bacillus stearothermophilus* spores were coated on a variety of materials to compare the fluorescent readout time. The *B. stearothermophilus* spores were obtained, as described in Example 1, and were suspended in ethanol and deposited at approximately $1 \times 10^6$ spores per $6.35 \times 28.58$ mm ($\frac{1}{4} \times \frac{9}{8}$ inch) strip of the following materials: polypropylene/rayon nonwoven web, commercially available as "Novonette® Nonwoven Fabric #149-190" from Kendall Fiber Products Division; nylon nonwoven web, commercially available as "Novonette® Nonwoven Fabric #149-000" from Kendall Fiber Products Division, Boston, MA; microporous hydrophobic film, commercially available as "Celgard® Microporous Hydrophobic Film 2500" from Celanese Separations Products, Charlotte, NC; microporous hydrophilic film, commercially available as "Celgard® Microporous Hydrophilic Film 3401" from Celanese Separations Products; aluminum foil commercially available from Reynolds, Metals Company, Richmond, VA; filter paper, commercially available as "S&S 591A Grade Filter Paper" from Schleicher & Schuell; filter paper, commercially available as "S&S 903 Grade Filter Paper" from Schleicher & Schuell; and glass fiber nonwoven web, commercially available as "Manniglas #1267 Nonwoven Glass Fiber Paper" from Manning Paper Company, Division of Hammermill Paper Co., Troy, NY. Ten microliters of the suspended spores, i.e., $1 \times 10^6$ spores, were also deposited in polypropylene vials of the same dimensions as those described in Example 1.

Devices utilizing the spore strips were assembled in accordance with Example 1, Device 1, and as illustrated in FIGS. 3 and 4, except that a 1.75 mm (11/16 inch) in diameter piece of polypropylene nonwoven scrim, commercially available as "0.5 oz Celestra ™ Nonwoven Polypropylene" from Crown Zellerback Corp., Camas, WA was sandwiched between the spore strip 46 and the bottom of the outer vial. This sandwich insured wetting of the spore strips with nutrient media when ampoule 48 is broken, since the scrim acts as a wick to draw nutrient media past the hydrophobic nylon web, microporous hydrophobic film, aluminum foil, or glass fiber nonwoven web. Devices utilizing the spore coated vials were assembled in accordance with Example 1, Device 1, except that the device contained no spore strip or barrier. Three unit batches of the indicators were exposed in the "Amsco Eagle ™ Model 2013 Steam Sterilizer" at 132° C. for 1.0, 1.5, 2.0,. 2.5 and 3.0 minutes. After exposure the ampoules containing the enzyme substrate solution and nutrient medium were crushed and the devices were incubated at 56° C. and checked for fluorescence using a longwave U.V. light (λ=366) commercially available as a "Blak-Lamp", Model UV L-21, from Ultraviolet Products, Inc., San Gabriel, CA., every 15 minutes for 1 hour, and then hourly for up to 6 hours. Incubation was continued for 24 hours, and the devices were read for growth (yellow) or no growth (purple).

The results are reported in Table VI.

TABLE VI

| Carrier Material | Exposure Time (minutes) | FLUORESCENCE Incubation Time (Minutes) at 56° C. Number Positive/3 Tested | | | | | | | | | Spore Growth at 24 hr. |
|---|---|---|---|---|---|---|---|---|---|---|---|
| | | 15 | 30 | 45 | 60 | 120 | 180 | 240 | 300 | 360 | |
| Polypropylene/ | 1.0 | 3 | 3 | 3 | 3 | 3 | 3 | 3 | 3 | 3 | 3 |
| rayon web | 1.5 | 3 | 3 | 3 | 3 | 3 | 3 | 3 | 3 | 3 | 3 |
| ("Novonette ® | 2.0 | 3* | 3* | 3* | 3* | 3* | 3* | 3* | 3* | 3* | 1 |
| Nonwoven | 2.5 | 0 | 0 | 0 | 0 | 0 | 0 | 0 | 0 | 0 | 0 |
| Fabric") | 3.0 | 0 | 0 | 0 | 0 | 0 | 0 | 0 | 0 | 0 | 0 |
| Microporous | 1.0 | 3 | 3 | 3 | 3 | 3 | 3 | 3 | 3 | 3 | 3 |
| hydrophobic | 1.5 | 3 | 3 | 3 | 3 | 3 | 3 | 3 | 3 | 3 | 3 |
| film ("Celgard ® | 2.0 | 0 | 0 | 0 | 0 | 2 | 2 | 3* | 3* | 3* | 2 |
| Microporous | 2.5 | 0 | 0 | 0 | 0 | 0 | 0 | 0 | 0 | 0 | 0 |
| Hydrophobic Film 2500") | 3.0 | 0 | 0 | 0 | 0 | 0 | 0 | 0 | 0 | 0 | 0 |
| Aluminum foil | 1.0 | 3 | 3 | 3 | 3 | 3 | 3 | 3 | 3 | 3 | 3 |
| | 1.5 | 3 | 3 | 3 | 3 | 3 | 3 | 3 | 3 | 3 | 3 |
| | 2.0 | 0 | 0 | 0 | 0 | 1* | 1* | 2* | 3* | 3* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Microporous | 1.0 | 3 | 3 | 3 | 3 | 3 | 3 | 3 | 3 | 3 | 3 |
| hydrophilic | 1.5 | 3 | 3 | 3 | 3 | 3 | 3 | 3 | 3 | 3 | 2 |
| film ("Celgard ® | 2.0 | 0 | 0 | 0 | 1* | 3* | 3* | 3* | 3* | 3* | 0 |
| Microporous | 2.5 | 0 | 0 | 0 | 0 | 0 | 0 | 0 | 0 | 0 | 0 |
| Hydrophobic Film 3401") | 3.0 | 0 | 0 | 0 | 0 | 0 | 0 | 0 | 0 | 0 | 0 |
| Nylon nonwoven | 1.0 | 3 | 3 | 3 | 3 | 3 | 3 | 3 | 3 | 3 | 3 |
| web ("Novonette ™ | 1.5 | 2 | 2 | 2 | 2 | 3 | 3 | 3 | 3 | 3 | 2 |
| Nonwoven fabric" | 2.0 | 3 | 3 | 3 | 3 | 3 | 3 | 3 | 3 | 3 | 3 |
| #149-000) | 2.5 | 0 | 0 | 0 | 0 | 0 | 2* | 2* | 2* | 2* | 0 |
| | 3.0 | 0 | 0 | 0 | 0 | 0 | 0 | 0 | 0 | 0 | 0 |
| Filter paper | 1.0 | 3 | 3 | 3 | 3 | 3 | 3 | 3 | 3 | 3 | 3 |
| ("S&S 903 Grade | 1.5 | 3 | 3 | 3 | 3 | 3 | 3 | 3 | 3 | 3 | 3 |
| Filter Paper") | 2.0 | 3* | 3* | 3* | 3* | 3* | 3* | 3* | 3* | 3* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Filter paper | 1.0 | 3 | 3 | 3 | 3 | 3 | 3 | 3 | 3 | 3 | 3 |
| ("S&S 591A Grade | 1.5 | 3 | 3 | 3 | 3 | 3 | 3 | 3 | 3 | 3 | 3 |
| Filter Paper") | 2.0 | 0 | 0 | 1* | 1* | 2* | 2* | 2* | 2* | 2* | 0 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Glass fiber web | 1.0 | 3 | 3 | 3 | 3 | 3 | 3 | 3 | 3 | 3 | 3 |
| ("Manniglas #1267 | 1.5 | 3 | 3 | 3 | 3 | 3 | 3 | 3 | 3 | 3 | 3 |
| Nonwoven Glass | 2.0 | 1 | 1 | 2* | 3* | 3* | 3* | 3* | 3* | 3* | 1 |
| Fiber Paper") | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |
| Polypropylene | 1.0 | 2 | 3 | 3 | 3 | 3 | 3 | 3 | 3 | 3 | 3 |
| vials | 1.5 | 2 | 2 | 3 | 3 | 3 | 3 | 3 | 3 | 3 | 3 |
| | 2.0 | 0 | 0 | 0 | 0 | 2 | 2 | 2 | 2 | 2 | 2 |
| | 2.5 | 0 | 0 | 0 | 0 | 0 | 0 | 0 | 0 | 0 | 0 |
| | 3.0 | 0 | 0 | 0 | 0 | 0 | 0 | 0 | 0 | 0 | 0 |

*Indicates one or more false positive reactions which appear to be the result of residual enzyme activity following spore inactivation in marginal sterilization cycles In all the indicators with spores coated on carriers that survived the steam exposure, spore survival (by enzyme activity was) detected within 15 minutes. The indicators where the spores were coated directly on the vials required up to two hours to detect all instances where there was active alpha-D-glucosidase, and therefore spore survival. This increased time until reliable readout is a result of the fact that in the spore-coated vial indicators, the entire volume of medium must be monitored for fluorescence. In contrast, with the devices which use spore strips and a barrier between the ampoule and the spore strip, only the spore strip is viewed for fluorescence. The barrier acts as a semi-permeable membrane to allow a small volume of media and enzyme substrate to contact the spore carrier. Reaction of the enzyme on any portion of the carrier with the enzyme substrate can be seen in a much shorter time, than can reaction of enzyme with the entire contents of the ampoule.

EXAMPLE 7

"ATCC 9372"*Bacillus subtilis* was grown overnight (16 hours) at 37° C. in tryptic soy broth. This culture was used to inoculate the surface of agar plates consisting of 8 g/l nutrient broth, 0.011 g/l manganese sulfate and 20 g/l agar at pH 7.2. The plates were incubated at 37° C. for 6 days and the spores were scraped from the plates and suspended in sterile distilled water. The spores were separated from the vegetative debris by centrifuging the suspension at 7000 rpm and 4° C. for 20 minutes. The supernatant was poured off and the spores were resuspended in sterile distilled water. This cleaning procedure was repeated several times.

The *Bacillus subtilis* spores were coated at a population of $1.0 \times 10^8$ on $6.35 \times 28.58$ mm "S&S 591A Grade Filter Paper" strips. Devices were assembled using these spore strips, as shown in FIGS. 3 and 4, and as described in Example 1, Device 1. Three unit batches of these devices were preconditioned at 54° C. and 50% relative humidity for 30 minutes. The devices were then exposed for 15, 30, 60 and 120 minutes, at 54° C. and 50% relative humidity, to 600 mg/l of ethylene oxide in a Steri-Vac TM 400B Gas Sterilizer", commercially available from 3M Co., St. Paul, MN, which had been modified in accordance with the "Association for the Advancement of Medical Instrumentation, Standard for BIER/EO Gas Vessels", AAMI BEOU-3/82. After exposure, the inner ampoules were removed from the devices and 0.67 ml of a solution which was identical to that contained in the inner ampoule, except that it contained 0.03 g/l of 2,3,5-triphenyl tetrazolium chloride (commercially available from ICN Pharmaceuticals Inc., Cleveland OH), instead of bromocresol purple pH indicator dye, and 0.1 g/l 4-methylumbelliferyl-beta-D-glucoside (commercially available from Sigma), in place of the 4-methylumbelliferyl-alpha-D-glucoside, was pipetted into the outer vial. The devices were incubated at 37° C. An ultraviolet light ($\lambda = 366$ nm) was used to illuminate the devices to visually detect fluorescence after 30 min., 60 min., 90 min., 120 min., 180 min., 240 min. and 300 min. of incubation. Additionally, spore growth, as indicated by a color change from colorless to red was determined visually after 24 and 168 hours of incubation. The results are reported in Table VII.

TABLE VII

| Ethylene Oxide Exposure | FLUORESCENCE Incubation Time (minutes) at 37° C. Number of positives/3 tested | | | | | | | Spore Growth | |
|---|---|---|---|---|---|---|---|---|---|
| | 30 | 60 | 90 | 120 | 180 | 240 | 300 | 24 hr. | 168 hr. |
| 0 | 3 | 3 | 3 | 3 | 3 | 3 | 3 | 3 | 3 |
| 15 | 0 | 0 | 3 | 3 | 3 | 3 | 3 | 3 | 3 |
| 30 | 0 | 0 | 0 | 0 | 3* | 3* | 3* | 0 | 0 |
| 60 | 0 | 0 | 0 | 0 | 0 | 3* | 3* | 0 | 0 |
| 120 | 0 | 0 | 0 | 0 | 0 | 0 | 0 | 0 | 0 |

*Indicates one or more false positive reactions which appear to be the result of residual enzyme activity following spore inactivation in marginal sterilization cycles.

Table VII illustrates that in the devices where the spore survived the 15 minute ethylene oxide exposure, the fluorescence that resulted from the reaction of active β-D-glucosidase with the 4-methylumbelliferyl-B-D-glucoside was visually detected after 90 minutes of incubation. The enzyme was completely inactivated after 120 minutes of ethylene oxide exposure, demonstrating that 120 minutes of ethylene oxide exposure is a complete and efficacious sterilization cycle. Some residual enzyme activity was detected after 3 and 4 hours of incubation in marginal sterilization cycles of 30 and 60 minutes.

EXAMPLE 8

"ATCC 9372" *Bacillus subtilis* spores obtained as described in Example 7, were coated at a population of $1.0 \times 10^8$, on $6.35 \times 28.58$ mm, "S&S 591A Grade Filter Paper" strips. Devices were assembled using these spore strips, shown in FIGS. 3 and 4 and as described in Example 1, Device 1. Three unit batches of the devices were preconditioned at 54° C. with 50% relative humidity for 30 minutes. The devices were then exposed for 15, 30, 60 and 120 minutes at 54° C. and 50% relative humidity to 600 mg/l of ethylene oxide in a "Steri-Vac TM 400B Gas Sterilizer", modified as described in Example 7. After exposure the spore strips were removed from the devices and were transferred to individual wells in a 96 well microtiter plate, commercially available as a "Dynatech MicroFLUOR TM System" from Dynatech Laboratories, Inc., Alexandria, VA. Each well contained 200 µl of a solution of 17 g/l bacteriological peptone, 0.17 g/l L-alanine, 0.03 g/l triphenyl tetrazolium chloride and 0.1 g/l 4-methylumbelliferyl-β-D glucoside. Three negative control wells in the plate contained the solution of nutrient medium and enzyme substrate without the spore strip. The plate was incubated at 37° C. and the fluorescence of each well was measured after 0, 60, 120, 180 and 240 minutes of incubation in a fluorometer, commercially available as a "3M FluoroFAST TM 96 Fluorometer" from 3M Company, St. Paul, MN. The results are reported in Table VIII, as an average of the relative fluorescence for the three wells.

TABLE VIII

| | AVERAGE RELATIVE FLUORESCENCE (in relative fluorescence units) | | | | |
|---|---|---|---|---|---|
| Exposure Time | Incubation Time in (minutes) at 37° C. | | | | |
| | 0 | 60 | 120 | 180 | 240 |
| 0 | 388 | 2329 | 5000 | 5000 | 5000 |
| 15 | 417 | 334 | 397 | 573 | 1016 |
| 30 | 409 | 321 | 325 | 373 | 438 |
| 60 | 401 | 309 | 296 | 299 | 324 |
| 120 | 404 | 312 | 292 | 292 | 297 |
| Negative control | 278 | 215 | 195 | 191 | 186 |

The results of Example 7 illustrate that *Bacillus subtilis* spores survive the 15 minute ethylene oxide exposure described in this Example, and are killed after at least a 30 minute exposure. As indicated by the well containing the spore strip exposed for 15 minutes, activity of the enzyme β-D-glucosidase, and, hence, survival of the *B. subtilis* organism, is indicated after 3 hours of incubation by an increase in relative fluorescence of at least 2.5 times the background level fluorescence of the negative control after 3 hours of incubation. Likewise, in the unexposed control, an increase of relative fluorescence greater than 2.5 times the background level fluorescence of the negative control, after only 1 hour of incubation, indicates enzyme activity and spore survival.

However, the strips exposed to ethylene oxide sterilization for at least 30 minutes, had relative fluorescence values of less than 2.5 times the negative control after 3 hours of incubation. Thus, indicating only residual enzyme activity and the lack of spore survival.

FIG. 7 is the graphic representation of the results reported in Table VIII. In the figure line A represents the device exposed for 15 minutes, line B represents the device exposed for 30 minutes, line C represents the device exposed for 60 minutes, line D represents the device exposed for 120 minutes and line E represents the negative control.

EXAMPLE 9

Figure 8:
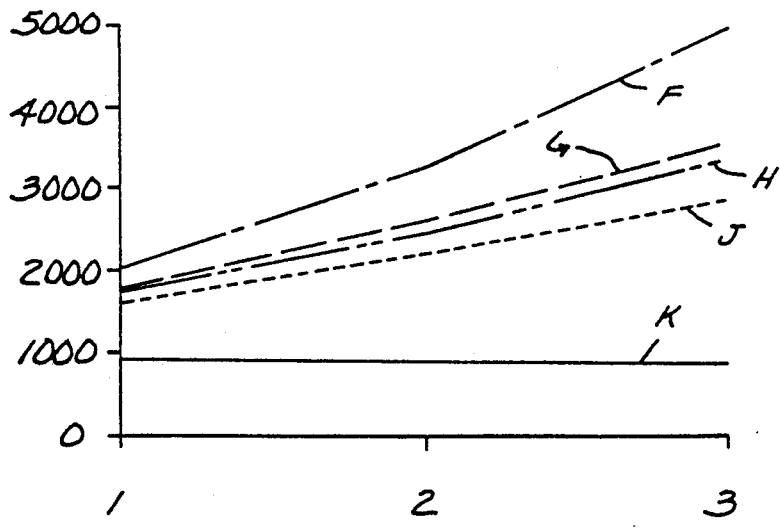
FIG. 8 is also a graphic representation of relative fluorescence versus incubation time for sterility indicators of this invention, after exposure to a sterilization cycle for varying periods of time.

"ATCC 9372" Bacillus subtilis spores, obtained as described in Example 7, were coated at a population of $1.0 \times 10^8$ on $6.35 \times 28.58$ mm ($\frac{1}{4} \times \frac{9}{8}$ inch) strips of "S&S 591A Grade Filter Paper". Devices were assembled using these spore strips, as shown in FIGS. 3 and 4 and as described in Example 1, Device 1. Three unit batches of the devices were preconditioned at 54° C. with 50% relative humidity for 30 minutes. The devices were then exposed for 15, 30, 60 and 120 minutes, at 54° C. and 50% relative humidity, to 600 mg/l of ethylene oxide in a "Steri-Vac TM 400B Gas Sterilizer", modified as described in Example 7. After exposure the spore strips, along with three identical unexposed spore strips were removed from the devices and were transferred to individual wells in a 96 well microtiter plate, commercially available as a "Dynatech MicroFLUOR TM System" from Dynatech Laboratories, Inc., Alexandria, Virginia. Each well contained 200 μl of a solution of 17 g/l bacteriological peptone, 0.17 g/l L-alanine, 0.03 g/l triphenyl tetrazolium chloride and 0.1 g/l methylumbelliferyl-alpha-D-arabinofuranoside, commercially available from Sigma. Three negative control wells in the plate contained the solution of nutrient medium and enzyme substrate without the spore strip. The plate was incubated at 37° C. and the fluorescence of each well was measured after 0, 60, 120, 180 and 240 minutes of incubation in a fluorometer, commercially available as a "3M FluoroFAST TM 96 Fluorometer" from 3M Company, St. Paul, MN. The results are recorded, as an average of the relative fluorescence for the three wells in FIG. 8, wherein average relative fluorescence is plotted against incubation time for wells containing spores exposed for 15, 30, 60 and 120 minutes, and the negative control. In the figure, F represents the device exposed for 15 minutes, G represents the device exposed for 30 minutes, H represents the device exposed for 60 minutes, J represents the device exposed for 120 minutes, and K represents the negative control.

The results of Example 7 illustrate that B. subtilis spores survive a 15 minute ethylene oxide exposure of the type described above, and are killed after at least a 30 minute exposure. In this example the alpha-D-arabinofuranosidase still had residual activity after the 120 minute cycle, which is considered a complete and efficacious sterilization cycle. This level of fluorescence is considered the background level, and any significant increase above this level indicates a sterilization failure. For example, after 3 hours of incubation, the difference in relative fluorescence units (RFU) between the strip exposed for 15 minutes and the strip exposed for 120 minutes is 2166. This difference is significant and indicates that 15 minutes is an incomplete sterilization cycle for the ethylene oxide conditions utilized. However, the difference between the strip exposed for 30 minutes and the strip exposed for 120 minutes is only 745 RFU. This difference is considered insignificant and indicates enzyme residual activity in marginal sterilization cycles of 30 minutes.

EXAMPLE 10

Bacillus stearothermophilus spores ("ATCC 7953"), obtained as described in Example 1, were suspended in distilled water, after one wash, at a population of $1 \times 10^8$ spores/ml. The following procedure was used to purify the enzyme alpha-D-glucosidase. The suspension (200 ml) was dialyzed against 2 l of a solution of 10 mM acetate buffer and 5 mM $CaCl_2$, pH 6.2, overnight at 4° C. Insoluble residues were then removed by centrifugation. The supernatant was fractionated with solid ammonium sulfate. The precipitates from 20%–60% ammonium sulfate were collected on a Buchner funnel containing a filter pad. The filter pad was prepared by passing a suspension (100 g/l) of "Celite ® Filter Aid", commercially available from Manville Specialty Product Group, Lompoc, CA. over two sheets of Whatman No. 1 filter paper. After filtration, the "Celite ® Filter Aid" pad was suspended in 20 ml of the solution of 10 mM acetate buffer and 5 mM $CaCl_2$, pH 6.2, and stirred for 4 hours at 4° C. "Celite ® Filter Aid" was removed from the soluble enzyme by filtration. The light brown enzyme solution was dialyzed overnight against 4 L of the solution of 10 mM acetate buffer and 5 mM $CaCl_2$ at 4° C. The dialyzed solution was removed from the dialysis tubing and filtered to remove insoluble debris.

The dialyzed solution was adjusted to pH 6.2 and two volumes of cold acetone ($-20°$ C.) were added with stirring. The acetone-enzyme solution was held at $-20°$ C. for 6 hours. The light brown precipitate was collected by gravity filtration at 4° C. and dissolved in 10 ml of the solution of 10 mM acetate buffer and 5 mM $CaCl_2$, pH 6.2. The light amber solution was adjusted to pH 5.5 by the addition of 0.1 M acetate buffer, pH 4.6. The solution was again treated with two volumes of cold acetone ($-20°$ C.) and stored at 20° C. overnight. The precipitate was collected by gravity filtration and dissolved in 10 ml of the solution of 10 mM acetate buffer and 5 mM $CaCl_2$, pH 6.2. The light amber solution was dialyzed for 48 hours against 4 L of a solution of 50 mM phosphate buffer and 5 mM EDTA, pH 6.2 (Buffer A), at 4° C. with complete buffer change every 24 hours.

Five ml of the dialyzed sample was loaded in a column (2.5×30 cm), packed with "DEAE-Sephadex ® Beads", commercially available from Pharmacia, Inc., Piscataway, NJ, and equilibrated with 50 mM phosphate buffer and 5 mM EDTA, pH 6.2. The column was washed successively with: a) 500 ml of Buffer A, and b) 200 ml of a linear 0–0.8 M NaCl gradient in Buffer A. The flow rate was kept at approximately 5 ml/60 min. The active fractions that appeared were collected and dialyzed for 48 hours against 4L of distilled water, with a complete change after 24 hours. The lyopholized fractions were suspended in a 3 ml of a solution of 150 mM phosphate buffer and 5 mM EDTA, pH 6.2 (Buffer B). This suspension was passed through a column (2.5×30 cm) packed with "Sephadex ® G-100 Beads", commercially available from Pharmacia, Inc., with Buffer B an approximate flow rate of 15 ml/60 min. The active fractions were collected and dialyzed against 4 L of distilled water. The dialyzed fractions were then lyopholized.

Seven 6.35×28.58 ($\frac{1}{4}$×$\frac{9}{8}$ inch) strips of "S&S 903 Grade Filter Paper" were saturated with a suspension of 0.02 M purified alpha-D-glucosidase in distilled water. Seven other paper strips, of the same type and dimension, were saturated with a 1×10$^6$ spores/ml solution of *B. stearothermophilus* spores, ("ATCC 7953"), obtained as described in Example 1, suspended in distilled water. All carrier strips were air dried overnight at ambient temperature (20° C.).

Devices were assembled using these spore strips as shown in FIGS. 3 and 4, and described in Example 1 as Device 1. These devices were exposed in a gravity displacement steam sterilizer, commercially available as an "Amsco Eagle TM Model 2013 Sterilizer" at 132° C. and 469.4 kg/cm$^2$ (33 psi) for 0.5, 1.0, 1.5, 2.0, 2.5 and 3.0 minutes. After exposure the inner ampoules containing the enzyme substrate and nutrient medium were crushed and the units were incubated at 56° C. for 24 hours. An ultraviolet light ($\lambda$=366 nm) was used to illuminate the vials for visually read fluorescence.

Relative fluorescence of each device was also measured using a 3M FluoroFAST TM 96 Fluorometer", at 366 nm. The results are recorded in Table IX.

TABLE IX

| Exposure Time (min) | FLUORESCENCE | | | |
|---|---|---|---|---|
| | Device with purified enzyme | | Device with spore strip | |
| | Observed[1] | Fluorometer (RFU) | Observed[1] | Fluorometer (RFU) |
| 0.0 | + | 3954 | + | 3182 |
| 0.5 | + | 1421 | + | 1876 |
| 1.0 | + | 860 | + | 1350 |
| 1.5 | + | 513 | + | 830 |
| 2.0 | + | 456 | + | 636 |
| 2.5 | − | 367 | − | 357 |
| 3.0 | − | 322 | − | 312 |

[1]"+" indicates fluorescence by visual observation while "−" indicates no fluorescence by visual observance.

The results in Table IX illustrate that the devices which employ the purified enzyme had the same visually observed fluorescence, and approximately the same measured fluorescence, as the devices employing *B. stearothermophilus*. Thus, this example illustrates that activity of the purified enzyme alone, not bound to the spore from which it is derived, is useful to detect spore survival.

What is claimed is:

1. A method for rapidly determining the effectiveness of a sterilization cycle, comprising the steps of:
   a) subjecting to said sterilization cycle of a source of active enzyme which provides a detectable amount of said enzyme, said enzyme having sufficient activity following a sterilization cycle which is sublethal to at least one test microorganism commonly used to monitor sterilization, to react with an effective amount of a substrate system for said enzyme to produce a detectable enzyme-modified product within less than twenty-four hours, yet said enzyme having activity which is reduced to "background" following a sterilization cycle which is lethal to said test microorganism;
   b) incubating said enzyme, following the completion of said sterilization cycle, with an effective amount of an enzyme substrate system capable of reacting with any residual active enzyme to produce a detectable enzyme-modified product, for a time period and under conditions sufficient to promote reaction of any enzyme remaining active with said substrate.

2. The method of claim 1 wherein said source of active enzyme is bacteria or fungus in either the spore or vegetative state.

3. The method of claim 1 wherein said active enzyme has been isolated from a microorganism.

4. The method of claim 1 wherein said enzyme is one which
   a) when subjected to a sterilization cycle which would be just sufficient to decrease the population of 1×10$^6$ test microorganisms to zero, as measured by lack of outgrowth of said microorganism, has activity equal to "background", as measured by reaction with an effective amount of an enzyme substrate system capable of reacting with said active enzyme to produce a detectable enzyme-modified product; and
   b) when subjected to a sterilization cycle sufficient to decrease the population of 1×10$^6$ of said test microorganisms by at least about 1 log, but less than about 6 logs, has activity greater than said background, as measured by reaction with an effective amount of said enzyme substrate system.

5. The method of claim 1 wherein said enzyme is selected from the group consisting of beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, beta-D-glucuronidase, N-acetyl-$\beta$-glucosaminidase, beta-D-cellobiosidase, alanine aminopeptidase, proline aminopeptidase, tyrosine aminopeptidase, leucine aminopeptidase, phenylalanine aminopeptidase and a fatty acid esterase derived from spore-forming microorganisms.

6. The method of claim 5 wherein said spore-forming microorganism is selected from the group consisting of *Candida, Bacillus, Clostridium* and *Neurospora* species of microorganisms.

7. The method of claim 2 wherein said source of active enzyme is *Bacillus stearothermophilus* or *Bacillus subtilis*.

8. The method of claim 1 wherein said enzyme substrate system is capable of reacting with said active enzyme in an aqueous reaction medium to produce an enzyme-modified product which differs in luminescence, fluorescence, color or radioactivity from said enzyme or enzyme substrate system.

9. The method of claim 8 wherein said enzyme substrate is fluorogenic.

10. The method of claim 8 wherein said enzyme substrate is chromogenic.

11. The method of claim 1 wherein said microorganism is selected from the group consisting of *Bacillus* and *Clostridia* species of microorganisms.

12. The method of claim 1 wherein said method further comprises subjecting a predetermined number of viable test microorganisms to said sterilization cycle along with said source of active enzyme, and the step
   c) incubating said test microorganisms following the completion of said sterilization cycle, with an aqueous nutrient medium capable, with incubation, of promoting growth of viable test microorganisms, and a detector material capable of undergoing a detectable change in response to growth of said test microorganisms, under conditions suitable to promote growth of said viable test microorganisms.

13. The method of claim 12 wherein said test microorganism is selected from the group consisting of *Bacillus stearothermophilus, Bacillus subtilis* and *Clostridium sporogenes*.

14. The method of claim 2 wherein said bacteria or fungi is one commonly used to monitor sterilization, and said method further includes the step
   c) incubating any of said bacteria or fungi which remains viable, following the completion of said sterilization cycle, with an aqueous nutrient medium capable, with incubation, of promoting growth of said viable bacteria or fungi, and a detector material capable of undergoing a detectable change in response to growth of said bacteria or fungi, under conditions suitable to promote growth of said viable bacteria or fungi.

15. The method of claim 14 wherein said bacteria or fungi is selected from the group consisting of *Bacillus stearothermophilus, Bacillus subtilis* and *Clostridium sporogenes*.

16. The method of claim 1 wherein said sterilization cycle is provided by saturated steam, dry heat, gas, liquid or radiation.

17. The method of claim 9 wherein said enzyme substrate system comprises an enzyme substrate selected from the group consisting of 4-methylumbelliferyl derivatives, 7-amido-4-methyl-coumarin derivatives, and diacetylfluorescein derivatives, which derivatives are capable of reacting with said enzyme to produce a fluorescent product, and fluoroescamine.

18. The method of claim 10 wherein said enzyme substrate system comprises an enzyme substrate selected from the group consisting of 5-bromo-4-chloro-3-indolyl derivatives, nitrophenyl derivatives, indoxyl derivatives, and phenolphtalein derivatives, which derivatives are capable of reacting with said enzyme to produce a colored product.

19. The method of claim 10 wherein said enzyme substrate system comprises a chromogenic reagent and a 1-napthyl, 2-naphthyl or naphthyl-AS-BI derivative capable of reacting with said enzyme and said chromogenic reagent to produce a colored product.

20. The method of claim 1 wherein said enzyme has sufficient activity following a sterilization cycle which is sublethal to at least one test microorganism commonly used to monitor sterilization, to react with said substrate system to produce a detectable enzyme-modified product within less than twelve hours.

21. The method of claim 20, wherein said enzyme, following the completion of the sterilization cycle, produces a detectable enzyme-modified product after incubation with said enzyme substrate system for a time period of twelve hours or less.

22. The method of claim 1 wherein said enzyme has sufficient activity following a sterilization cycle which is sublethal to at least one test microorganism commonly used to monitor sterilization, to react with said substrate system to produce a detectable enzyme-modified product within less than eight hours.

23. The method of claim 22, wherein said enzyme, following the completion of the sterilization cycle, produces a detectable enzyme-modified product after incubation with said enzyme substrate system for a time period of eight hours or less.

24. The method of claim 1 wherein said enzyme has sufficient activity following a sterilization cycle which is sublethal to at least one test microorganism commonly used to monitor sterilization, to react with said substrate system to produce a detectable enzyme-modified product within less than three hours.

25. The method of claim 24, wherein said enzyme, following the completion of the sterilization cycle, produces a detectable enzyme-modified product after incubation with said enzyme substrate system for a time period of three hours or less.

* * * * *